United States Patent
Bowman et al.

(10) Patent No.: US 11,497,870 B2
(45) Date of Patent: Nov. 15, 2022

(54) SYSTEMS AND METHODS FOR ESTIMATING FLOW IN POSITIVE AIRWAY PRESSURE THERAPY

(71) Applicant: SOMNETICS INTERNATIONAL, INC., Fridley, MN (US)

(72) Inventors: Bruce R. Bowman, Eden Prairie, MN (US); John R. Hanson, Falcon Heights, MN (US)

(73) Assignee: SOMNETICS INTERNATIONAL, INC., Fridley, MN (US)

( * ) Notice: Subject to any disclaimer, the term of this patent is extended or adjusted under 35 U.S.C. 154(b) by 1901 days.

(21) Appl. No.: 15/040,040

(22) Filed: Feb. 10, 2016

(65) Prior Publication Data
US 2016/0243325 A1 Aug. 25, 2016

Related U.S. Application Data

(60) Provisional application No. 62/119,888, filed on Feb. 24, 2015.

(51) Int. Cl.
*A61M 16/00* (2006.01)

(52) U.S. Cl.
CPC .... *A61M 16/0066* (2013.01); *A61M 16/0069* (2014.02); *A61M 16/026* (2017.08); *A61M 2016/0027* (2013.01); *A61M 2205/15* (2013.01); *A61M 2205/3365* (2013.01); *A61M 2205/50* (2013.01); *A61M 2205/502* (2013.01)

(58) Field of Classification Search
CPC .......... A61M 16/0066; A61M 16/0069; A61M 16/026; A61M 2016/0027; A61M 2205/15; A61M 2205/3365; A61M 2205/50; A61M 2205/502

See application file for complete search history.

(56) References Cited

U.S. PATENT DOCUMENTS

| | | | |
|---|---|---|---|
| 4,957,107 A | 9/1990 | Sipin | |
| 5,313,937 A | 5/1994 | Zdrojkowski | |
| 5,433,193 A | 7/1995 | Sanders et al. | |
| 5,517,983 A | 5/1996 | Deighan et al. | |
| 5,535,738 A * | 7/1996 | Estes | A61M 16/024 128/204.21 |

(Continued)

FOREIGN PATENT DOCUMENTS

EP 1 649 887 A2 4/2006

OTHER PUBLICATIONS

U.S. Appl. No. 62/119,888, filed Feb. 24, 2015, Bowman et al.

*Primary Examiner* — Kendra D Carter
(74) *Attorney, Agent, or Firm* — Mueting Raasch Group

(57) ABSTRACT

A system adapted to regulate pressure of a flow of breathable gas generated by a motorized blower fan. The system may include a flow estimation analyzer adapted to receive a speed signal representative of a speed of the fan and estimate a parameter representative of the flow of breathable gas (e.g., a flow rate of the breathable gas). The parameter may be determined by inputting the speed signal into a function (e.g., an equation, matrix, or lookup table), which may be selected from a plurality of predetermined functions. The predetermined function may be selected based upon a specific characteristic of the speed signal as identified at the time of estimation of the parameter representative of flow.

26 Claims, 11 Drawing Sheets

(56) References Cited

U.S. PATENT DOCUMENTS

| | | |
|---|---|---|
| 5,645,053 A | 7/1997 | Remmers et al. |
| 5,694,926 A * | 12/1997 | DeVries .............. A61M 16/125 |
| | | 128/204.21 |
| 5,715,812 A | 2/1998 | Deighan et al. |
| 5,740,795 A | 4/1998 | Brydon |
| 5,803,066 A | 9/1998 | Rapoport et al. |
| 5,868,133 A * | 2/1999 | DeVries .............. A61M 16/125 |
| | | 128/204.18 |
| 6,237,593 B1 | 5/2001 | Brydon |
| 6,283,119 B1 | 9/2001 | Bourdon |
| 6,332,463 B1 * | 12/2001 | Farrugia .............. A61M 16/00 |
| | | 128/204.18 |
| 6,571,795 B2 | 6/2003 | Bourdon |
| 6,968,842 B1 | 11/2005 | Truschel et al. |
| 7,168,429 B2 | 1/2007 | Matthews et al. |
| 7,588,031 B2 | 9/2009 | Truschel et al. |
| 7,827,988 B2 | 11/2010 | Matthews et al. |
| 7,938,113 B2 | 5/2011 | Weinstein et al. |
| 7,938,114 B2 | 5/2011 | Matthews et al. |
| 8,136,521 B2 | 3/2012 | Matthews et al. |
| 8,353,289 B2 | 1/2013 | Farrugia et al. |
| 2004/0016430 A1 * | 1/2004 | Makinson .............. A61M 16/10 |
| | | 128/203.12 |
| 2006/0000475 A1 | 1/2006 | Matthews et al. |
| 2008/0041383 A1 | 2/2008 | Matthews et al. |
| 2008/0251071 A1 * | 10/2008 | Armitstead .............. H02P 29/02 |
| | | 128/202.22 |
| 2010/0319697 A1 | 12/2010 | Farrugia et al. |
| 2011/0120462 A1 * | 5/2011 | Tatkov .............. A61M 16/1075 |
| | | 128/203.14 |
| 2012/0152252 A1 | 6/2012 | Matthews et al. |
| 2013/0118496 A1 | 5/2013 | Truschel et al. |
| 2014/0007878 A1 * | 1/2014 | Armitstead .............. A61B 5/083 |
| | | 128/204.23 |
| 2015/0165146 A1 | 6/2015 | Bowman et al. |

\* cited by examiner

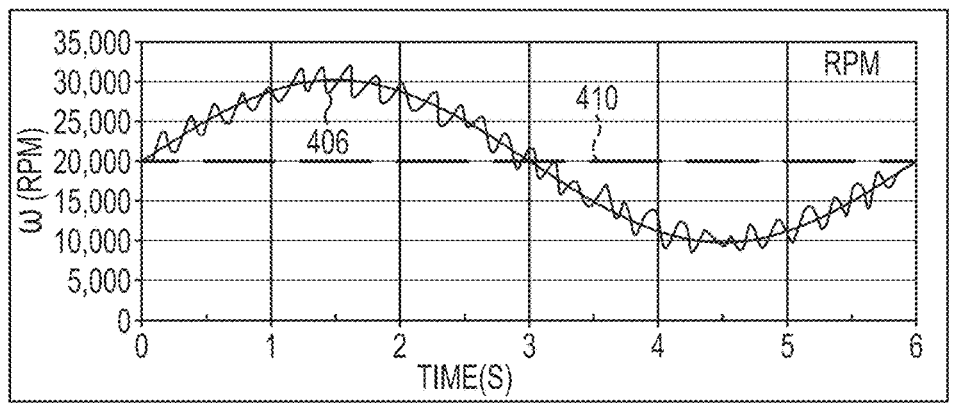
Fig. 5A
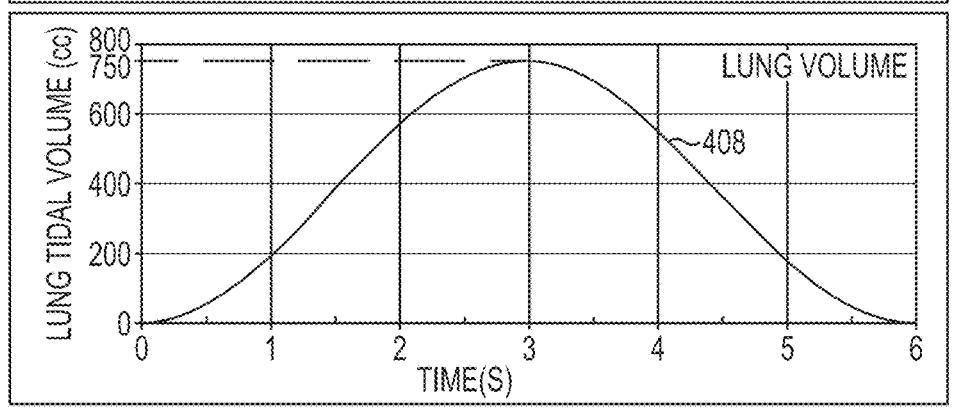
Fig. 5B
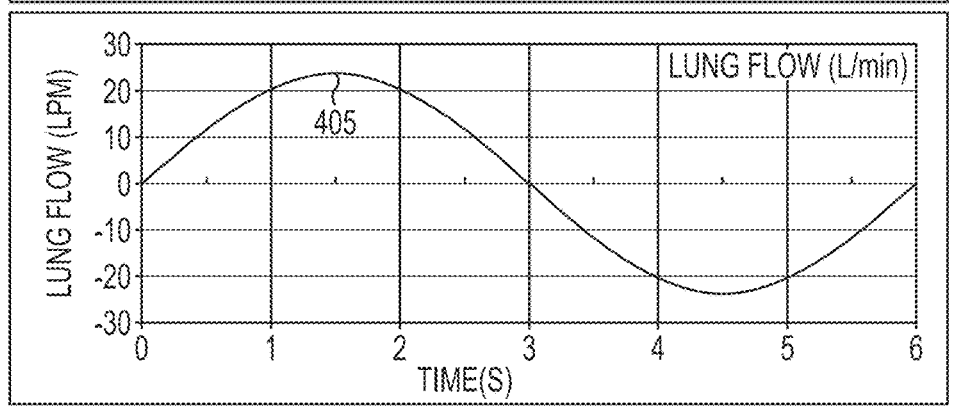
Fig. 5C
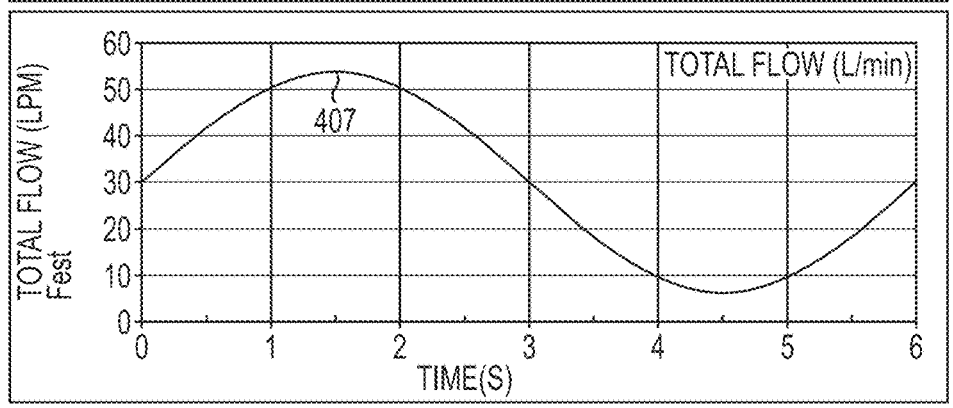
Fig. 5D
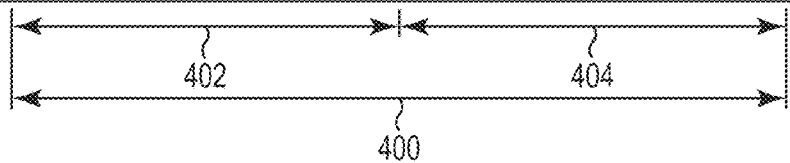

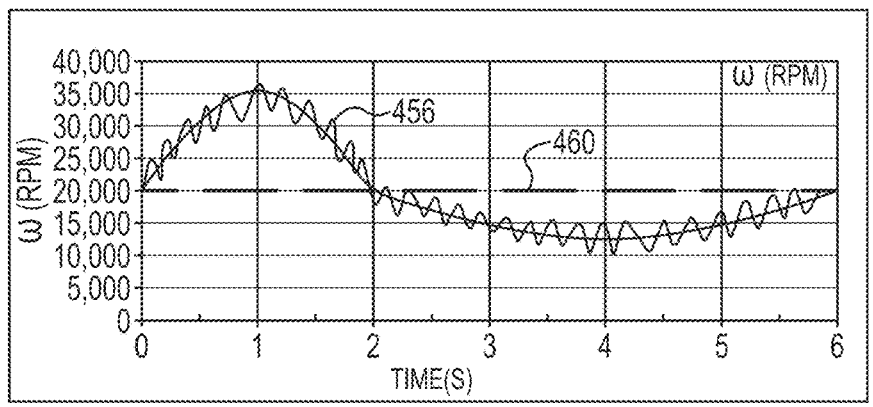
Fig. 6A
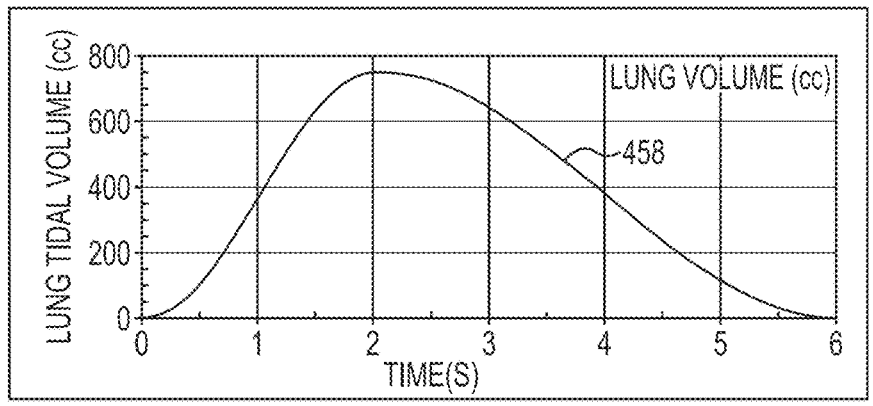
Fig. 6B
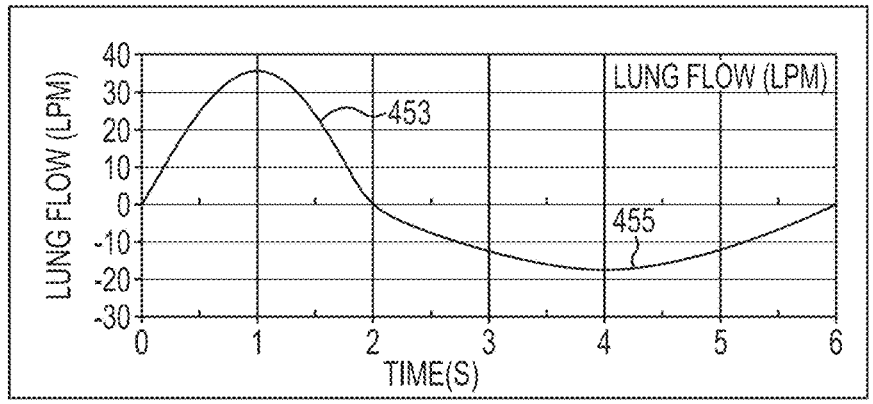
Fig. 6C
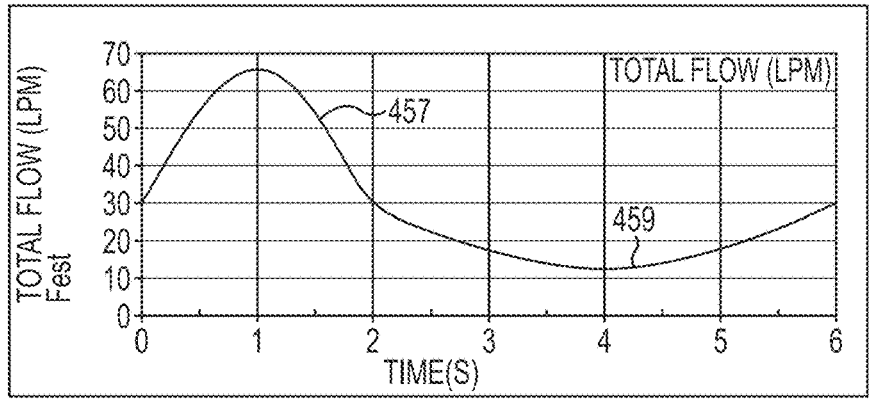
Fig. 6D
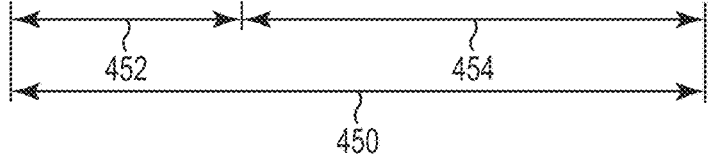

SYSTEMS AND METHODS FOR ESTIMATING FLOW IN POSITIVE AIRWAY PRESSURE THERAPY

This application claims the benefit of U.S. Provisional Application No. 62/119,888, filed Feb. 24, 2015, which is incorporated herein by reference in its entirety.

Positive airway pressure apparatus and systems, including systems and methods for estimating flow within a positive airway pressure apparatus.

BACKGROUND

Positive airway pressure (PAP) therapies are frequently used in the treatment of, among other ailments, obstructive sleep apnea, complex sleep apnea, asthma, bronchitis, chronic obstructive pulmonary disease (COPD), snoring, and congestive heart failure. These therapies typically provide a flow of pressurized gas (e.g., typically air, but may be most any gas or gas-vapor mixture including, for example, oxygen and medicinal vapors) to pressurize the airway of a user to a pressure in the range of 4-30 centimeters (cm) of water ($H_2O$) (e.g., often about 4-20 cm $H_2O$) or more. Depending upon the particular therapy, a variable or a constant pressure therapy may be administered to the user to reduce or eliminate airway occlusions (or to otherwise treat acute or chronic respiratory failure) that necessitated the use of the therapy. For instance, continuous positive airway pressure (CPAP) may provide a generally continuous pressure throughout the user's breathing cycle. Bi-level positive airway pressure (Bi-PAP) may provide a variable pressure in coordination with the user's inspiration and expiration efforts. In more advanced systems, auto-titration positive airway pressure (Auto-PAP) may regulate the therapy apparatus based on the level of breathing assistance the user may require at any given point during therapy. Still further, adaptive servo-ventilation may be used to treat complex sleep apnea syndrome, which can be identified when central apneas or periodic breathing occur during a reduction of obstructive events with positive airway pressure.

Regardless of the particular therapy, positive airway pressure apparatus typically includes at least a blower unit and a mask. A delivery hose may also be included to connect the blower unit to the mask, wherein the hose and mask may together define a delivery conduit between the blower and the user. The blower unit may rest on a bedside table or floor adjacent the bed (or in the bed), or alternatively, may attach to the user. The blower may typically include a fan or impeller connected to an output shaft of a motor. A controller regulates the motor to control fan speed and thus therapy pressure. The mask is configured to be secured relative to the user's head in such a way as to form a generally air-tight seal with the user's airway. As a result, the fan may generate a flow of pressurized gas that is delivered to the airway via the delivery conduit.

To control the pressurized gas, pressure within the system is typically monitored (e.g., via a pressure sensor or transducer located near the outlet of the blower or in the mask) and regulated by the controller in a way that maintains a desired pressure profile during breathing.

As those of skill in the art may appreciate, it is sometimes beneficial to accurately measure flow of the pressurized gas to or from the user during therapy. Monitoring (and potentially storing data regarding) flow parameters may, for example, assist in: detecting unintentional mask leaks; monitoring user compliance; detecting transitions between inspiration and expiration (e.g., for Bi-PAP); and otherwise detecting breath anomalies such as apneas and hypopneas.

Typically, flow is measured by a pneumotachometer (i.e., a differential pressure transducer measuring pressure difference across a flow restriction) located within the delivery conduit. Electrical signals representing flow may then be transmitted to the controller. While effective, such flow measuring transducers can increase the overall size, cost, and complexity of the positive airway pressure apparatus.

SUMMARY

Embodiments are described that may overcome these and other issues by providing, in one embodiment, a positive airway pressure apparatus including: a blower adapted to generate a flow of breathable gas, the blower including a motor and a fan rotatable by the motor; a sensor associated with the blower, the sensor adapted to detect a rotational speed of the fan and generate a speed signal representative of the rotational speed of the fan; a controller adapted to measure pressure of the flow of breathable gas; and an analyzer in communication with the controller. The analyzer is adapted to receive the speed signal and estimate a parameter representative of the flow of breathable gas, the parameter determined by inputting the speed signal into a function selected from a plurality of predetermined functions, wherein each of the plurality of predetermined functions corresponds to one of a plurality of characteristics associated with the rotational speed of the fan.

One or more aspects may be additionally included in the apparatus above, singularly or in any combination, to produce additional embodiments. For example, in one aspect, each of the plurality of predetermined functions includes an equation, a matrix, or a lookup table. In another aspect, the sensor adapted to detect the rotational speed of the fan includes a tachometer, Hall effect sensor, a motor coil voltage or current sensor, an electromagnetic field sensor, or an optical sensor. In yet another aspect, a characteristic of the plurality of characteristics includes a baseline speed of the fan, wherein the baseline speed is, in one embodiment, determined by averaging the speed of the fan over a preceding period of time, and wherein the average speed of the fan over the preceding period of time may be time-weighted. In still another aspect, the baseline speed of the fan is determined by the speed of the fan during an apnea. In still yet other aspects, a characteristic of the plurality of characteristics includes: an instantaneous speed of the fan; a rotational speed of the fan indicative of inspiration or a rotational speed of the fan indicative of expiration; a detected increase or detected decrease in the rotational speed of the fan; and/or a detected rate of increase or detected rate of decrease in the rotational speed of the fan. In one aspect, the detected rate of increase (or decrease) in the rotational speed of the fan includes a first rate of increase (or decrease) and a second rate of increase (or decrease), wherein a first function of the plurality of predetermined functions is utilized for the first rate of increase (or decrease), and a second function of the plurality of predetermined functions, different than the first function, is utilized for the second rate of increase (or decrease). In still another aspect, a characteristic of the plurality of characteristics includes a pressure of the flow of breathable gas.

In another embodiment, a method is provided for estimating a flow parameter of a positive airway pressure apparatus. The method includes: producing a flow of breathable gas with a blower, the blower including a motor and a fan powered by the motor; generating a speed signal proportional to a rotational speed of the fan; delivering the speed signal to a flow estimation analyzer; determining, with the analyzer, a first characteristic of the speed signal; selecting, with the analyzer, a first function from a plurality of predetermined functions based upon the first characteristic of the speed signal, wherein each function of the plurality of predetermined functions is adapted to correlate the speed signal to a flow rate of the flow of breathable gas; estimating, with the first function, the flow rate of the flow of breathable gas.

One or more aspects may be additionally included in the method above, singularly or in any combination, to produce additional embodiments. For example, in one aspect, the method may also include: determining, with the analyzer, a second characteristic of the speed signal; selecting, with the analyzer, a second function of the plurality of predetermined functions based upon the second characteristic; and estimating with the second function, the flow rate of breathable gas. In another aspect, determining the first or second characteristic of the speed signal includes determining the first or second characteristic when the flow of breathable gas is constant. In still another aspect, determining the first or second characteristic of the speed signal includes determining the first or second characteristic when the flow of breathable gas varies. In yet other aspects, determining the first or second characteristic of the speed signal includes: determining whether the speed signal is indicative of inspiration or expiration; and/or determining a rate of increase or a rate of decrease of the speed of the fan. In still yet another aspect, determining the first or second characteristic of the speed signal includes determining an average or baseline speed of the fan during a previous period of time. Determining the baseline speed of the fan may include determining whether the baseline speed of the fan is within at least a first range or a second range. In still another aspect, detecting a mask leak is based, at least in part, upon the estimated flow rate. In another aspect, detecting an apnea or hypopnea is based, at least in part, upon the estimated flow rate. In yet other aspects, estimating the flow rate includes: estimating the flow rate using a linear relationship between the flow rate and the speed signal; estimating the flow rate using a non-linear relationship between the flow rate and the speed signal; estimating the flow rate using one or a plurality of independent linear (and/or non-linear) relationships between the flow rate and the speed signal; and/or estimating the flow rate using a lookup table of the flow rate based upon the speed signal. In yet other aspects, generating the speed signal includes: measuring the speed of the fan with a sensor; and/or measuring a coil voltage or current of the motor.

In yet another embodiment, a positive airway pressure apparatus is provided that includes: a blower adapted to generate a flow of breathable gas, the blower including a motor and a fan rotatable by the motor; a sensor associated with the blower, the sensing device adapted to detect a rotational speed of the fan and generate a speed signal representative of the rotational speed of the fan; a controller adapted to measure pressure of the flow of breathable gas; and an analyzer in communication with the controller. The analyzer is adapted to receive the speed signal and estimate a parameter representative of the flow of breathable gas, the parameter determined by inputting the speed signal into a function selected from one or more predetermined functions, wherein each of the predetermined functions corresponds to one or more characteristics associated with the rotational speed of the fan.

The above summary is not intended to describe each embodiment or every implementation possible. Rather, a more complete understanding of various illustrative embodiments will become apparent and appreciated by reference to the following Detailed Description of Exemplary Embodiments and claims in view of the accompanying figures of the drawing.

BRIEF DESCRIPTION OF THE VIEWS OF THE DRAWING

Exemplary embodiments will be further described with reference to the figures of the drawing, wherein:

FIGS. 5A-5D are exemplary graphs (having a common time axis) of a simulated breath having an inspiration-expiration ratio of 1:1, wherein: FIG. 5A illustrates blower (motor) speed versus (v.) time; FIG. 5B illustrates lung tidal volume v. time; FIG. 5C illustrates estimated lung flow v. time; and FIG. 5D illustrates total flow v. time;

FIGS. 6A-6D are exemplary graphs (again having a common time axis) of a simulated breath having an inspiration-expiration ratio of 1:2, wherein: FIG. 6A illustrates blower (motor) speed v. time; FIG. 6B illustrates lung tidal volume v. time; FIG. 6C illustrates estimated lung flow v. time; and FIG. 6D illustrates total flow v. time;

Figure 1:
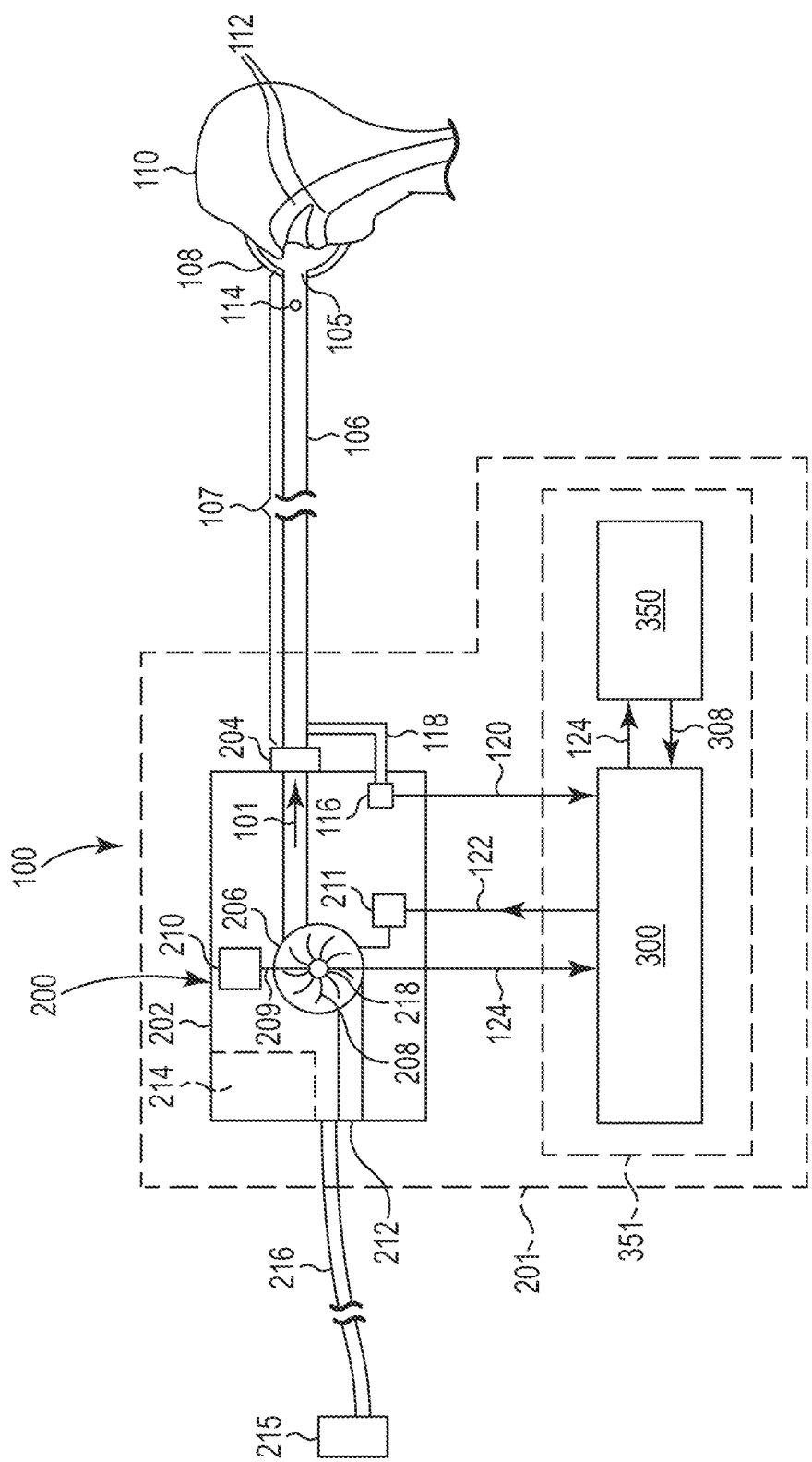
FIG. 1 is a diagrammatic illustration of a positive airway pressure apparatus in accordance with one embodiment, the apparatus comprising an analyzer, e.g. (flow estimation analyzer), a controller, and a blower with a motor.

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments. The lack of illustration/description of such structure/components in a particular figure is, however, not to be interpreted as limiting the scope of any embodiment in any way.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments that may be practiced.

Embodiments described herein are directed generally to positive airway pressure apparatus and methods and to flow estimation devices and methodologies for use with the same. While described herein primarily in the context of the treatment of sleep-disordered breathing, those of skill in the art will realize other embodiments are equally applicable to most any assisted respiration or ventilation system, and in fact to most any positive airway pressure system. These and other variations, combinations, and modifications will be apparent to those skilled in the art, and it should be understood that this disclosure is not limited to the illustrative embodiments set forth herein.

All headings provided herein are for the convenience of the reader and should not be used to limit the meaning of any text that follows the heading, unless so specified. Moreover, unless otherwise indicated, all numbers expressing quantities, and all terms expressing direction/orientation (e.g., vertical, horizontal, parallel, perpendicular, etc.) in the specification and claims are to be understood as being modified in all instances by the term "about."

It is noted that the terms "comprises" and variations thereof do not have a limiting meaning where these terms appear in the accompanying description and claims. Further, "a," "an," "the," "at least one," and "one or more" are used interchangeably herein. Additionally, relative terms such as "left," "right," "front," "fore," "forward," "rear," "aft," "rearward," "top," "bottom," "side," "upper," "lower," "above," "below," "horizontal," "vertical," and the like may be used herein and, if so, are from the perspective observed in the particular figure. These terms are used only to simplify the description, however, and not to limit scope in any way.

With reference to the drawings, wherein like reference numerals designate like parts and assemblies throughout the several views, FIG. 1 diagrammatically illustrates an exemplary, non-invasive, positive airway pressure (PAP) apparatus 100. The PAP apparatus 100 may include a flow generator or blower 200 adapted to generate or otherwise produce a flow of breathable gas 101. The blower 200 may include an outlet 204 that is coupled to a first or proximal end of a delivery or air hose 106. A second or distal end of the hose 106 may be connected to an inlet 105 of a user interface 108. The user interface 108 is illustrated generically, but is understood to include most any interface that seals effectively to a user 110 (e.g., to the user's face) in such a way that gas delivered to the user interface may be communicated to an airway 112 of the user without excessive unintentional leakage. For example, the user interface could be a face mask that covers one or both of the user's mouth and nose; a nares pillow seal; or any similar device. For simplicity, the user interface may be referred to herein simply as a "mask" without limitation.

As used herein, the terms "air," "gas," and "fluid" are understood to include most any gas or gas-vapor combination. For example, the gas provided by the blower may include air, oxygen, water vapor, medicinal vapor, and combinations thereof. For simplicity, the terms air, fluid, and gas may, unless otherwise indicated, be used interchangeably herein without limitation.

The hose 106 and mask 108 may together define a delivery conduit 107 adapted to provide pressurized gas from the blower 200 to the airway 112 of the user. The delivery conduit 107 may include one or more vents or ports 114 to provide what is referred to as an "intentional leak" or "intentional vent leak," described in more detail below. The intentional leak may assist in purging carbon dioxide from the system during expiration to minimize the carbon dioxide that may be re-breathed. While, the actual size of the intention leak may vary from system-to-system and/or from mask-to-mask, the minimum size is generally designed to adequately flush carbon dioxide even when the PAP device is operating at the minimum allowable pressure, e.g., 4 cm $H_2O$. Leaks that are larger than necessary to accomplish this goal, however, may result in placing excessive load on the motor/blower. Typically, the magnitude of intentional leak may be expressed in terms of the size or cross-sectional area of the port(s) 114, with "leaks" of 12 square millimeters ($mm^2$) to 22 $mm^2$ being common, though other sizes are certainly possible.

To produce the desired pressurized gas within the delivery conduit 107, the blower 200 may include a blower housing 202 forming a volute 206 containing an impeller or fan 208. An electric motor 210, such as a brushless DC motor, may couple to and rotate the fan. As the fan rotates, it draws gas (e.g., ambient air) in via an inlet 212 of the housing where it is then compressed by the fan and expelled through the outlet 204. By controlling the rotational speed of the fan 208, the pressure of the gas within the delivery conduit 107 may be controlled to provide the desired treatment pressure to the user.

The apparatus 100 may further include an electronic (e.g., microprocessor-based) controller 300 that may, among other tasks, modulate or otherwise control a speed of the motor 210 (and, accordingly, a speed of the fan 208), thereby regulating the treatment pressure of the flow of breathable gas. The apparatus 100 may, in one embodiment, include a microprocessor-based motor controller 211. The controller and other components of the apparatus 100 may be powered by either an onboard power supply (e.g., a battery 214) or a remote power supply 215 (e.g., AC or DC source) connected via an electric cord 216.

The controller 300 could be separate from (but electrically connected to) the blower 200 (e.g., the controller could have its own battery and/or power supply), or could alternatively be contained within a unified housing as represented by the broken line housing 201 in FIG. 1. The electrical connections between the controller 300 and the blower 200, as well as any other connections described herein between the various components of the system, may be diagrammatically illustrated as physical (i.e., wired) connections. However, it is contemplated that these connections could also be made via wireless (e.g., radio frequency, infrared, etc.) technology.

The apparatus 100 may further include a pressure sensor or transducer 116. The pressure transducer 116 may be positioned within the housing 202, the controller 300, the analyzer 350, or at most any location along the delivery conduit 107. In the illustrated embodiment, the transducer 116 is located within the housing 202 and connected to the delivery conduit with a sense line or conduit 118. The pressure transducer 116 may produce an electrical signal $P_{act}$ representative of the actual, measured pressure in the delivery conduit 107. $P_{act}$ may then be transmitted to the controller 300 via an electrical signal line 120 (once again, the signal line 120, like other interconnections of the apparatus 100, could be wired or wireless). As further described below, the controller 300 may compare $P_{act}$ to a commanded pressure $P_{com}$ and, via closed-loop control, modulate a commanded motor speed $S_{com}$ to the motor controller 211 via a command line 122. As a result, the apparatus 100 may maintain a desired (e.g., constant) pressure in the delivery conduit 107 regardless of variations (e.g., inspiration, expiration, changes in unintentional leak, etc.) in flow.

In the illustrated embodiment, the apparatus 100 may further be able to detect a rotational speed of the motor/fan and generate a speed signal representative of (proportional to) the rotational speed. This signal will be referred to herein as speed signal ω. In one embodiment, rotational speed is determined by measuring the speed of an output shaft 209 of the motor 210 (and thus the fan 208) in, for example, revolutions/minute (RPM) with a sensor 218 associated with the blower. The sensor 218 used to determine the speed signal ω may be most any sensor including, for example, a tachometer, one or more Hall-effect sensors, an electromagnetic sensor, or most any other electrical, mechanical, or optical sensor that is capable of generating an electrical signal proportional to the rotational speed of the motor 210/fan 208. In other embodiments, the speed signal ω may be determined by measuring coil voltage or current of the motor 210, which may be proportional to the motor/fan speed. Motor speed may also be determined by a motor controller or other electronic component that controls the drive of the motor and also provides, directly or indirectly, continuous motor speed information. As used herein, speed signal ω is understood to be synonymous with the actual speed of the motor 210/fan 208/shaft 209.

Figure 2:
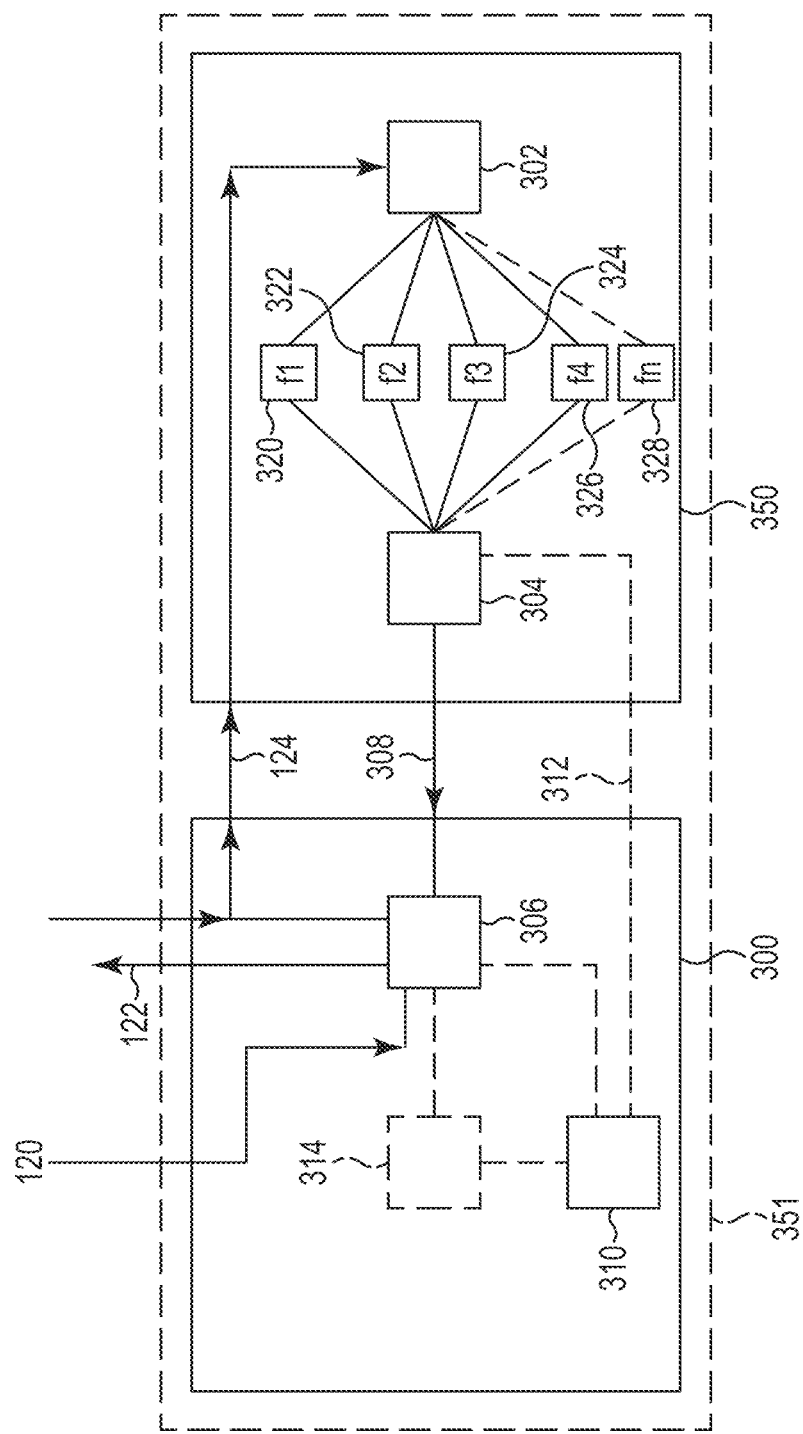
FIG. 2 is an enlarged diagrammatic view of the exemplary flow estimation analyzer and controller of FIG. 1.

Once measured (e.g., by the sensor 218) or otherwise determined (e.g., by coil voltage or current), speed signal ω may be delivered to and received by an electronic flow estimation analyzer 350 (also referred to herein as merely "analyzer 350"), e.g., by an electrical signal line 124 as shown in FIG. 1. The speed signal may also be delivered to and/or pass through the controller 300 as illustrated in FIGS. 1 and 2. The speed signal ω may provide the system 100 with additional functionality as further described below.

In the illustrated embodiment, the analyzer 350 is separate from, but in communication with, the controller 300. However, in other embodiments, the analyzer 350 may be integrated with the controller 300, or at least contained within a unified housing 351 as illustrated in FIGS. 1 and 2.

As described above, the controller 300 may, at least in some embodiments, be configured to regulate or maintain a constant system pressure, regardless of flow variations, by measuring pressure (e.g., via the pressure transducer 116) and adjusting motor speed. For example, when flow in the apparatus 100 is equal to zero, (e.g., when no leakage or breathing occurs), the speed of the motor (and thus the speed signal ω) will be proportional to the pressure within the conduit 107 (as measured by the transducer 116).

However, when a load is then placed on the system (e.g., by intentional leak via the port(s) 114), the motor speed will increase (to maintain pressure) in proportion to the flow of gas passing through the conduit. That is, when no breathing occurs, the motor speed may be relatively constant and proportional to the total gas flow resulting from intentional (and unintentional) leak.

When breathing loads are introduced (e.g., during breathing), flow (and therefore motor speed) will no longer be static, but will instead vary in synchronization with the user's inspiration and expiration. For example, when inspiration occurs, the motor speed will increase in order to maintain the desired pressure, and decrease during expiration.

This relationship between the speed of the motor/fan (represented by speed signal ω) and gas flow through the delivery conduit 107 allows the controller 300 to maintain a specific set treatment pressure (as measured at the transducer 116 via signal $P_{act}$) during operation. It may further indirectly provide a signal representative of system flow without requiring a dedicated flow sensor. Moreover, the inventor(s) have recognized that, in the context of a PAP apparatus, this relationship is dynamic. That is, the relationship between flow and motor speed may change based upon a variety of factors such as, for example, one or more characteristics of the motor speed that may vary during the treatment period (and that may vary based on geographic locations/elevation). It is believed that a more accurate estimate of flow may be realized by first analyzing these characteristics.

FIG. 2 is an enlarged diagrammatic view of the exemplary controller 300 and analyzer 350. As shown in this view, the analyzer 350 may include a signal processor adapted to estimate a parameter representative of the flow of breathable gas (e.g., the flow rate) and generate a signal representative of flow that is based upon the measured motor speed (e.g., based upon the speed signal ω), as well as upon other factors that may influence the estimation calculation. Stated alternatively, the analyzer 350 may conduct a motor speed-to-air flow transformation that may produce a signal that is then delivered to the controller 300 as a surrogate for an air flow signal. In this illustrated embodiment, the speed signal ω (provided via the signal line 124) may serve as an input to a decision element 302. The decision element 302 may analyze the speed signal ω and, based upon one or more characteristics determined from this analysis, select a specific function, e.g., from a plurality of predetermined functions (e.g., function 1 ("f1") as represented by block 320, function 2 ("f2") as represented by block 322, function 3 ("f3") as represented by block 324, function 4 ("f4") as represented by block 326, etc.) to relate the speed signal ω to the flow of gas within the system.

For example, for a given set of static system parameters such as gas resistance characteristics, motor/blower characteristics, gas density characteristics (e.g., type of gas, gas temperature, humidity level, and altitude), and dynamic system parameters (e.g., breathing-related parameters such as target pressure, actual pressure, and/or pressure delivery errors), the decision element 302 may analyze a characteristic of the speed signal ω (e.g., a baseline speed of the motor (described in more detail below), actual speed of the motor, rate of change of the motor speed, whether the motor is accelerating or decelerating, etc.) that will be used to determine flow. Based upon this analysis, the analyzer 350 (e.g., decision element 302) may select one of the plurality of the predetermined functions (e.g., 320, 322, 324, or 326) to then calculate flow. Each of the predetermined functions may differ in how it correlates the speed signal ω to gas flow within the system. Exemplary characteristics of the speed signal ω, as well as exemplary predetermined functions, are described in more detail below. While illustrated herein as providing four functions (320, 322, 324, and 326), those of skill in the art will appreciate that the apparatus 100 may utilize most any number of functions as indicated by function $f_n$ at 328. In some embodiments, a larger (or, in other embodiments, a smaller) number of predetermined functions may improve the accuracy of flow estimation. In other embodiments, multiple functions may be combined (e.g., using mathematical relationships between functions) into a single function (or into a reduced number of functions) that may provide a suitable transfer function relating motor/fan speed to system flow.

Once the predetermined function is selected by the decision element 302, a signal processing or calculation element 304 of the analyzer 350 may calculate a value or signal $F_{est}$ representative of the estimated flow provided by the blower 200 at any given time by applying the selected predetermined function to the speed signal ω. $F_{est}$ may then be transmitted to a processing unit 306 (e.g., a microprocessor, micro-controller, or other processing element) of the controller 300 via an input line 308, wherein the processing unit may utilize $F_{est}$, if desired, to adjust $S_{com}$ (via command line 122). In addition or alternatively, $F_{est}$ may be provided to a memory 310 via an input line 312, thereby allowing storage of flow data for subsequent use by the controller(s) and/or for subsequent interrogation by a clinician. Other components, e.g., an input/output element 314, may also be provided and may communicate with other elements of the apparatus (e.g., with the memory 310, the processing unit 306, and/or a display that provides information to the user or clinician).

In practice, the processing unit 306 may be programmed to utilize the signal $F_{est}$ to determine anomalies in the user's breath that may indicate a sleep-disordered breathing event such as an apnea, hypopnea, flow-limitation, snoring, or the like. By analyzing flow information, the controller 300 may be capable of altering the speed of the motor (e.g., via $S_{com}$ over command line 122), and thus the pressure within the system, to better assist the user in restoring normal breathing patterns. The controller 300 may also be configured to record (e.g., in the memory 310): various information regarding user compliance (e.g., breathing waveforms); and breathing events that occur during therapy (including, for example, the occurrence of an apnea, hypopnea, flow-limited breathing, and snoring) for subsequent reporting to a clinician.

As described herein, the controller 300 may include the processor 306, memory 310, and other components necessary or beneficial to controller operation. The memory 310 may include computer-readable instructions that, when executed, e.g., by the processor 306, cause the controller to perform various functions. The memory 310 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. The memory 310 may, as stated above, also be able to record user compliance data and breathing events. While shown as both being incorporated into the controller 300, the memory 310 and the processor 306 could be contained in one or more separate modules.

The processor 306 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 306 may include multiple components, such as any combination of one or more microprocessors, one or more controllers, one or more DSPs, one or more ASICs, and/or one or more FPGAs, as well as other discrete or integrated logic circuitry. The functions attributed to the controller 300/processor 306 herein may be embodied as software, firmware, hardware, or any combination thereof.

In one or more embodiments, the exemplary systems and methods described herein may be implemented using one or more computer programs using a computing apparatus such as the processor 306 and memory 310. Program code and/or logic described herein may be applied to input data to perform functionality described herein and generate desired output commands and/or information. The output may be applied as an input to one or more other devices (e.g., the analyzer 350) and/or methods as described herein or as would be applied in a known fashion. In view of the above, it will be readily apparent that controller 300 functionality as described herein may be implemented in any manner known to one skilled in the art.

Moreover, while described herein as a separate component, the analyzer 350 may, in some embodiments, merely be a function executed by the controller 300. As a result, the decision element 302 and calculation element 304 may be functions executed by the processor 306 and memory 310 of the controller 300. In other embodiments wherein the analyzer 350 is a distinct, separate component from the controller 300, the analyzer may include a processor that embodies the "decision element" and the "calculation element," as well as memory and other components. Accordingly, the analyzer 350 may, in application, merely be another controller similar to the controller 300. As a result, the preceding paragraphs describing embodiments of the memory and processor of the controller 300 may also find application to the analyzer 350 as well.

With this brief introduction, exemplary systems and methods for estimating parameters representative of flow (e.g., $F_{est}$) in a PAP system (such as the apparatus 100 illustrated in FIG. 1) will now be described.

As indicated above, the apparatus 100 may provide a particular system pressure for a specific motor speed. However, this relationship is dependent upon the leak, both intentional and unintentional, within the system.

For example, the size of the intentional leak may affect both a baseline motor speed as well as the pressure provided. As will become evident below, identifying the baseline speed may be beneficial to the accuracy of flow estimation. "Baseline speed," as used herein, refers to the motor/fan speed (e.g., as represented by the speed signal ω) when no breathing occurs (e.g., during an apnea). That is, baseline speed is generally the motor/fan speed (at a given set treatment pressure) when the system is subject only to intentional and unintentional leaks. In reality, other factors (e.g., blower and motor efficiencies, altitude, gas density, gas temperature, etc.) may also affect the baseline speed.

Figure 3:
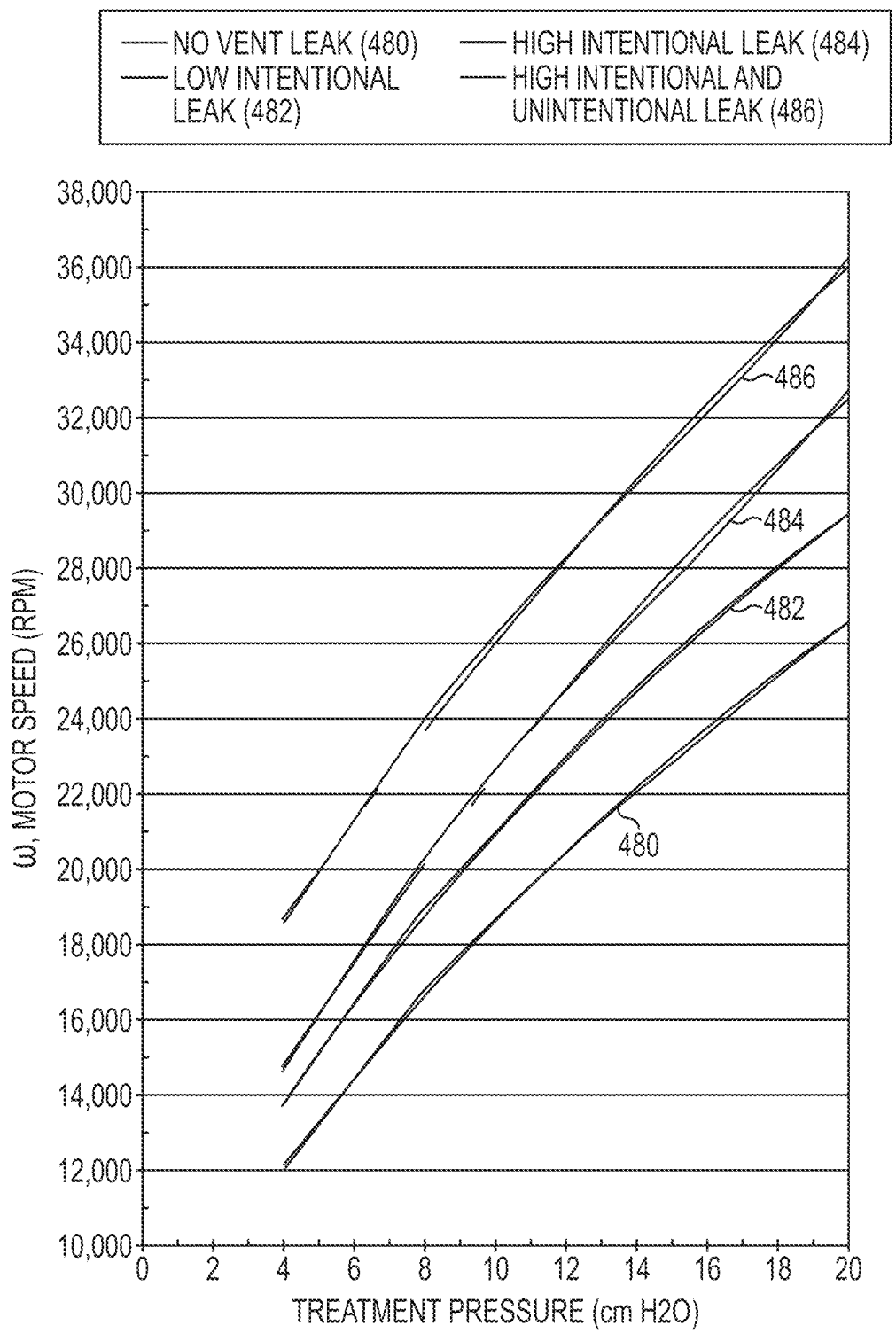
FIG. 3 is an exemplary graph illustrating motor speed versus treatment pressure for different levels of intentional and unintentional leak for an exemplary PAP apparatus in accordance with one embodiment of the disclosure.

FIG. 3 depicts an exemplary graph of motor speed ω (in RPM) versus treatment pressure (in cm $H_2O$) for various leak levels for a particular motor fan and system configuration under exemplary environmental and gas conditions. The leak levels illustrated are typical of low and high intentional leaks that may be common with commercially-available PAP masks. As shown in this example, baseline motor speed is indicated over a treatment pressure range of 4 cm $H_2O$ to 20 cm $H_2O$ when: the apparatus 100 is in a zero-leak configuration (curve 480); the apparatus includes a low intentional leak, e.g., 12 $mm^2$ (curve 482); the apparatus includes a high intentional leak, e.g., 22 $mm^2$ (curve 484); and the apparatus includes the high intentional leak plus a high unintentional leak (curve 486, assuming a high unintentional leak of 24 liters/minute (LPM)).

Unintentional leaks may develop as a result of improper attachment of the mask and/or dislodgement of the mask during sleep. As shown in FIG. 3, the effects of unintentional leaks may place a potentially substantial load on the PAP apparatus. For example, adding a high unintentional leak of 24 LPM to the high intentional leak scenario may increase the motor speed from 14,800 RPM to 18,700 RPM (at 4 cm $H_2O$), and from 32,500 RPM to 36,100 RPM (at 20 cm $H_2O$) to maintain the desired treatment pressure.

Figure 4:
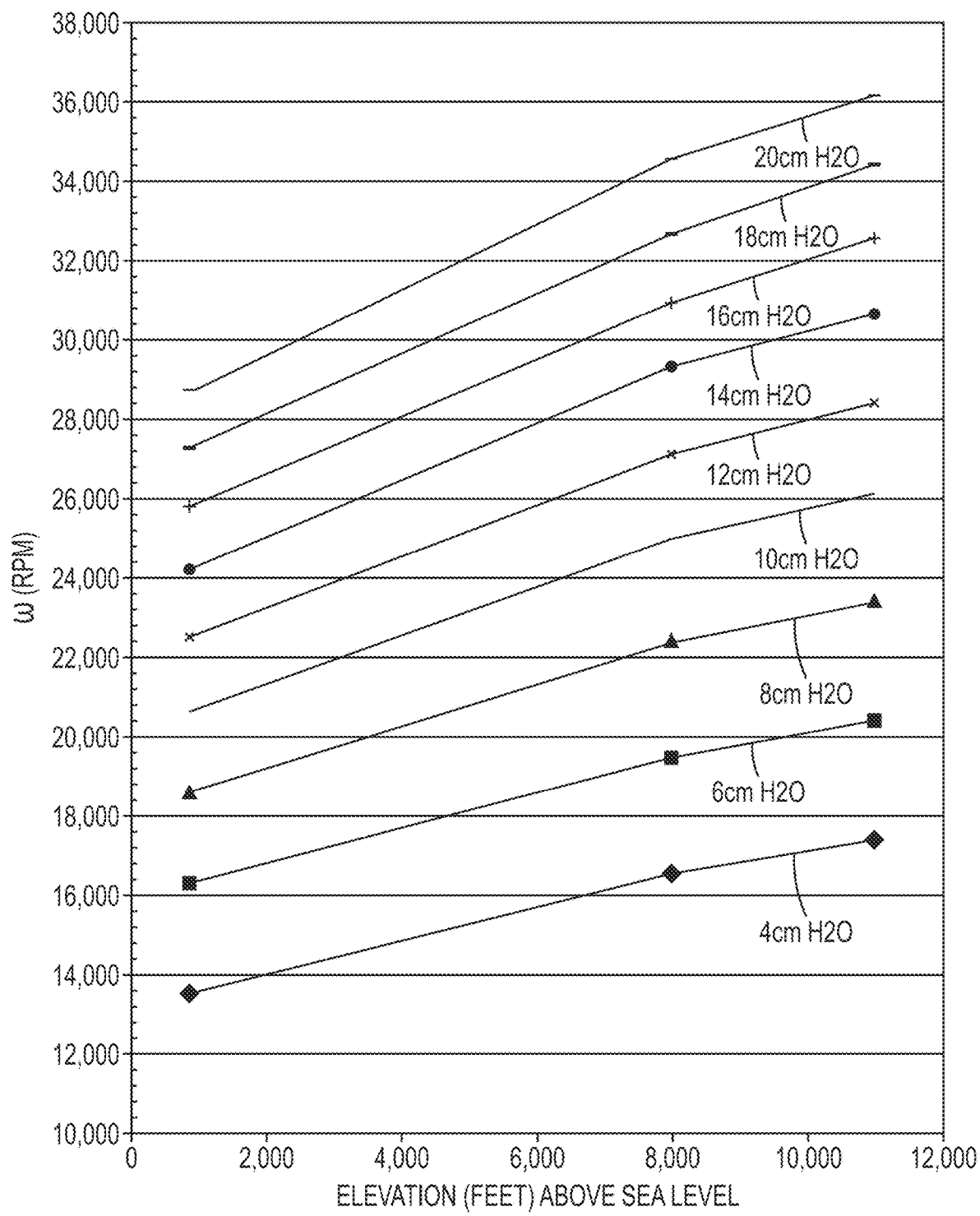
FIG. 4 is an exemplary graph illustrating motor speed versus elevation for various treatment pressures for an exemplary PAP apparatus in accordance with one embodiment of the disclosure (wherein the curves illustrated, from bottom to top, are for: 4, 6, 8, 10, 12, 14, 16, 18, and 20 cm $H_2O$)

In addition to changes in leak, altitude may also affect motor (baseline) speed. For example, FIG. 4 illustrates an exemplary graph of motor speed (speed signal $\omega$) versus elevation above sea level (for the exemplary PAP apparatus 100) at various treatment pressures. As shown in this figure, to supply a constant pressure (assuming a 12 $mm^2$ intentional leak) of 4 cm $H_2O$ at an elevation of 2,000 feet above sea level, the motor would rotate at approximately 14,000 RPM. However, the same PAP apparatus would need to increase motor speed to approximately 15,900 RPM at an elevation of 6,000 feet above sea level to maintain the same pressure of 4 cm $H_2O$. Other curves in FIG. 4 are provided to illustrate corresponding elevational influences on motor speed for other system pressures (e.g., 6, 8, 10, 12, 14, 16, 18, and 20 cm $H_2O$).

The effects of leak and altitude on motor speed as depicted in FIGS. 3 and 4, respectively, are relatively constant for a given set of environmental and gas conditions (i.e., with the exception of a change in unintentional leak, the motor speed necessary to maintain a constant treatment pressure, at a particular altitude and intentional leak, will remain constant). However, as stated above, breathing adds yet another load on the system. Furthermore, breathing load, by definition, varies over the course of a breath cycle (e.g., motor speed, as described below, increases above baseline speed during inspiration (see inspiration portion 402 in FIG. 5A) and decreases below baseline speed during expiration (see expiration portion 404 in FIG. 5A)).

With reference now to FIGS. 5A-5D, a simulated breath cycle 400 is illustrated (the same breath cycle is reflected in each of FIGS. 5A-5D, with each figure sharing a common, identical time axis) for a user connected to the exemplary PAP apparatus 100 providing a constant pressure. As shown in these figures, the breath cycle 400 includes one inspiration portion 402 (e.g., the portion of the breath cycle 400 spanning from 0-3 seconds (s)) followed by one expiration portion 404 (e.g., the portion of the breath cycle 400 spanning from 3-6 s) and assumes a sinusoidal breathing pattern with an inspiration-expiration ratio (I:E ratio) of 1:1 (reference numerals 400, 402, and 404 are explicitly identified in FIG. 5D only, but apply also to FIGS. 5A-5C). In this instance, the raw speed signal $\omega$ measured by the speed sensor (or otherwise determined by the system), which may be somewhat noisy, is represented by curve 406 in FIG. 5A. In some embodiments, the speed signal $\omega$ may be electronically filtered to yield a smooth (best-fit) speed signal $\omega$ curve as is also shown in this figure. In some embodiments, some components of this signal may not be filtered (or only slightly filtered) to maintain sufficiently rapid detection of speed changes that the analyzer 350 may need to provide accurate flow estimations. For example, some functions (e.g., f1, f2, f3, f4, fn of FIG. 2) may use a lessor filtered speed signal $\omega$, while other functions may use a more filtered speed signal $\omega$. As one of skill may appreciate, filtering of the speed signal $\omega$ may be accomplished by either analog circuitry or digital processing.

As the PAP apparatus 100 is, in one embodiment, configured as a constant pressure device, the speed of the fan 208 (and thus the speed signal $\omega$) during breathing may generally oscillate, at least during sinusoidal breathing periods, about an average speed (e.g., the baseline speed 410). As flow is proportional to speed, flow may also oscillate in a sinusoidal fashion as also shown. For instance, in the example shown in FIG. 5C, lung flow 405 may oscillate between a maximum of 24 LPM (on inspiration) and −24 LPM (on expiration). A total flow curve 407, which may additionally account for unintentional and intentional leak, may shift the flow curve upwardly as shown in FIG. 5D (this example assumes a combined intentional and unintentional leak of 30 LPM, yielding a peak flow during inspiration of 54 LPM, and a peak flow during expiration of 6 LPM). Finally, FIG. 5B illustrates a curve 408 representing lung tidal volume (which is illustrated, for example, as peaking at 750 cubic centimeters (cc)). As one of skill in the art will appreciate, integration of the inspiration and expiration flow (i.e., volume as represented by curve 408) over a single breath cycle (e.g., cycle 400) is typically about zero or, at the very least, very near zero over a series of completed breath cycles.

Like the breath cycle 400, FIGS. 6A-6D illustrates another simulated breath cycle 450 (once again, the same breath cycle 450 is reflected in each of FIGS. 6A-6D, with each figure sharing the same, identical time axis). As with the breath cycle 400, the breath cycle 450 has one inspiration portion 452 (e.g., the portion of the breath cycle 450 shown between 0 and 2 s) followed by one expiration portion 454 (e.g., the portion of the breath cycle 450 shown between 2 and 6 s). Once again, the actual reference numerals 450, 452, and 454 are explicitly identified in FIG. 6D only, but apply also to FIGS. 6A-6C. FIG. 6A illustrates the speed signal $\omega$ (assuming a constant pressure) represented by curve 456 (both filtered and unfiltered signals illustrated). It is noted, however, unlike the breath cycle 400, the breath cycle 450 represents breathing with a more typical asymmetric I:E ratio, e.g., a ratio of 1:2 having a maximum inspiration lung flow 453 of 35 LPM, and a maximum expiration lung flow 455 of −18 LPM (see FIG. 6C). Assuming once again a leak total of 30 LPM, this would yield a total flow curve as shown in FIG. 6D, with a peak flow during inspiration 457 of 65 LPM, and a peak flow 459 during expiration of 12 LPM. A lung tidal volume is again assumed to be about 750 cc as represented by curve 458 (see FIG. 6B). Once again, the integral of inspiratory and expiratory flow (e.g., volume as represented by lung tidal volume curve 458) over a single breath cycle would typically be equal, or nearly equal, to zero. Unlike the breath cycle 400 illustrated in FIGS. 5A-5D, the flow for the breath cycle 450 shown in FIG. 6A-6D does not oscillate symmetrically about a baseline speed 460 as the I:E ratio is now asymmetric.

While FIGS. 5A-5D and 6A-6D illustrate sinusoidal breathing for both inspiratory and expiratory portions of an exemplary breath cycle, actual breathing waveforms may vary substantially even during normal breathing. Moreover, breathing waveforms are even more likely to deviate from sinusoidal patterns with patients that suffer from sleep disordered breathing. Nonetheless, while lung tidal volume may not always return to zero for each breath cycle, it will generally be at or near zero when evaluated over multiple breath cycles. As described below, accurately determining the baseline speed in any of these scenarios may allow the analyzer 350 (see FIG. 2) to effectively remove the influence of extraneous (non-breath-related) flow factors. As a result, RPM deviations from the baseline speed during system operation (e.g., when breathing is occurring) may be, by definition, attributable to breathing activity.

Various methods may be utilized to assist in determining the baseline speed. For instance, in one embodiment, baseline speed may be determined by averaging motor/fan speed (e.g., via the speed signal ω) over a preceding period of time, knowing that, as stated above, integration of inspiratory flow and expiratory flow (the volume) over that period of time (assuming an equal number of inspirations and expirations) would be at or near zero. Baseline speed could also be estimated based upon the selection of a particular system configuration (e.g., certain mask, hose, intentional leak, system pressure setting, etc.). Still further, baseline speed could be averaged at the time of a detected apnea. The average baseline speed may, in some embodiments, be a time-weighted average (either linear or non-linear).

With continued reference to FIGS. 5A-5D and 6A-6D, the shape of the curve 406 (and 456) is presented as generally continuous. However, the shape of these curves may be altered by a sleep disordered breathing event (e.g., the occurrence of an apnea or hypopnea). When sleep disordered breathing occurs, the event may be addressed by algorithms in the controller 300 (e.g., based upon flow input received from the analyzer 350) that detect such occurrences and cause the apparatus 100 to initiate corrective actions, e.g., raise the system pressure in an attempt to correct the breathing anomaly.

While the baseline speed 410 (or 460) should remain generally constant during the treatment period, it may change in certain circumstances. For example, a sustained increase in leak (e.g., the development of a gross mask leak, which could be indicated by sustained increased flow rate) could shift the baseline speed upwardly over time. Moreover, pressure changes such as may occur when a PAP apparatus is configured as an Auto-PAP device may result in the baseline shifting upwardly when the pressure increases and shifting downwardly when the pressure decreases.

As described above and shown in FIGS. 5A-5D and 6A-6D, estimated total flow $F_{est}$ is proportional to the speed signal ω, i.e., $F_{est}$ may be described as a predetermined function of ω as shown in Equation (1) below.

$$F_{est} = f(\omega) \quad (1)$$

Stated yet another way, $F_{est}$ may be determined, e.g., by the analyzer 350 (see FIG. 2), based upon the speed signal ω, a parameter that is already measured/determined by the apparatus 100 at any given moment.

The functional relationship between $F_{est}$ and ω may be expressed in various ways. For instance, $F_{est}$ could be equal to some predefined constant multiplied by the motor speed (e.g., by the speed signal ω), i.e., a linear relationship. In another embodiment, calculating $F_{est}$ may be done with a series of linear or non-linear, piecemeal equations wherein, for example, the functional relationship (the utilized equation) could change at different RPM levels (e.g., every 1,000 RPM, a different equation could be used).

In yet another embodiment, $F_{est}$ could be expressed as a non-linear (e.g., polynomial) function such as that provided in Equation (2) below, wherein $A_x$, $B_x$, $C_x$, and $D_x$ are empirically determined constants.

$$F_{est} = A_x(\omega)^3 + B_x(\omega)^2 + C_x(\omega) + D_x \quad (2)$$

$A_x$, $B_x$, $C_x$, and $D_x$ may have different values for each of the plurality of predetermined functions so that each of the plurality of predetermined functions may uniquely correspond to one of a plurality of characteristics associated with the rotational speed of the motor 210/fan 208 (e.g., associated with the speed signal ω). Other equations, including other higher or lower order polynomial equations, may also be used to define the relationship between $F_{est}$ and ω. Moreover, while the polynomial of Equation (2) may be appropriate for one or more predetermined functions, other predetermined functions may utilize other equations such as a linear or non-linear (e.g., an exponential, quadratic, differential or partial differential equation) function, or a combination of linear and non-linear functions, to relate $F_{est}$ to the speed signal ω.

Some embodiments may further employ a time delay between: measuring of ω and/or calculating of $F_{est}$; and changing motor speed to allow for system response delays. The amount of delay may be based on how much change or rate of change in motor speed takes place, or if the motor speed change exceeds certain thresholds.

Figure 7:
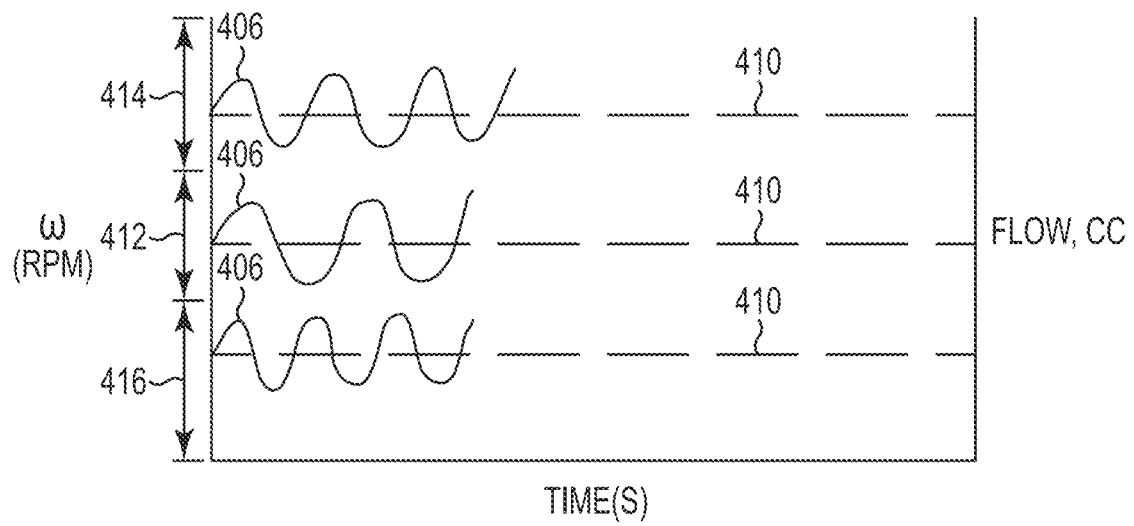
FIG. 7 is an exemplary graph of motor speed and flow versus time, wherein a characteristic of motor speed, e.g., a baseline speed of the motor, is shown as being within one of a plurality of ranges.

Providing a plurality of predetermined functions may be advantageous. As an example, one potential issue with calculating $F_{est}$ via a single predetermined function (e.g., Equation (2)) is that, while the constants $A_x$, $B_x$, $C_x$, and $D_x$ may be accurate for a certain range of motor speeds (or other characteristics), they may be less accurate for other ranges. $A_x$, $B_x$, $C_x$, and $D_x$ may, therefore, be empirically determined to be equal to $A_1$, $B_1$, $C_1$, and $D_1$, respectively, to provide an accurate result for $F_{est}$ when the baseline speed 410 of the speed signal ω is within a first range 412 as shown in FIG. 7. However, when the baseline speed 410 falls within a second (e.g., higher) range 414, the constants $A_x$, $B_x$, $C_x$, and $D_x$ may be empirically determined to be equal to $A_2$, $B_2$, $C_2$, and $D_2$, respectively (at least one of which may be different than $A_1$, $B_1$, $C_1$, and $D_1$, respectively). Similarly, when the baseline speed 410 is in a third (e.g., lower) range 416, the constants $A_x$, $B_x$, $C_x$, and $D_x$ may be empirically determined to be equal to $A_3$, $B_3$, $C_3$, and $D_3$, respectively, of which again at least one may be different than both corresponding variables: $A_1$, $B_1$, $C_1$, and $D_1$; and $A_2$, $B_2$, $C_2$, and $D_2$.

Thus, a more accurate estimation of flow may be obtained by selecting the function (the functional relationship between the speed signal ω and $F_{est}$) from a plurality of predetermined functions, wherein each function is selected based upon a particular identified characteristic of the speed signal ω. For instance, where the characteristic of the speed signal ω is the baseline speed as described above, the predetermined function utilized may be selected based upon which predetermined range the baseline speed falls within. That is, where the characteristic of the speed signal ω is the baseline speed, the decision element 302 (see FIG. 2) may determine which predefined range (e.g., 412, 414, or 416 of FIG. 7) the baseline speed falls within. Based upon this determination, the decision element 302 may select the function (e.g., 320, 322, 324, or 326) appropriate for the detected baseline speed.

As stated above, while described in the context of three distinct baseline speed ranges 412, 414, and 416, such a configuration is exemplary only as most any number of ranges are possible.

Figure 8:
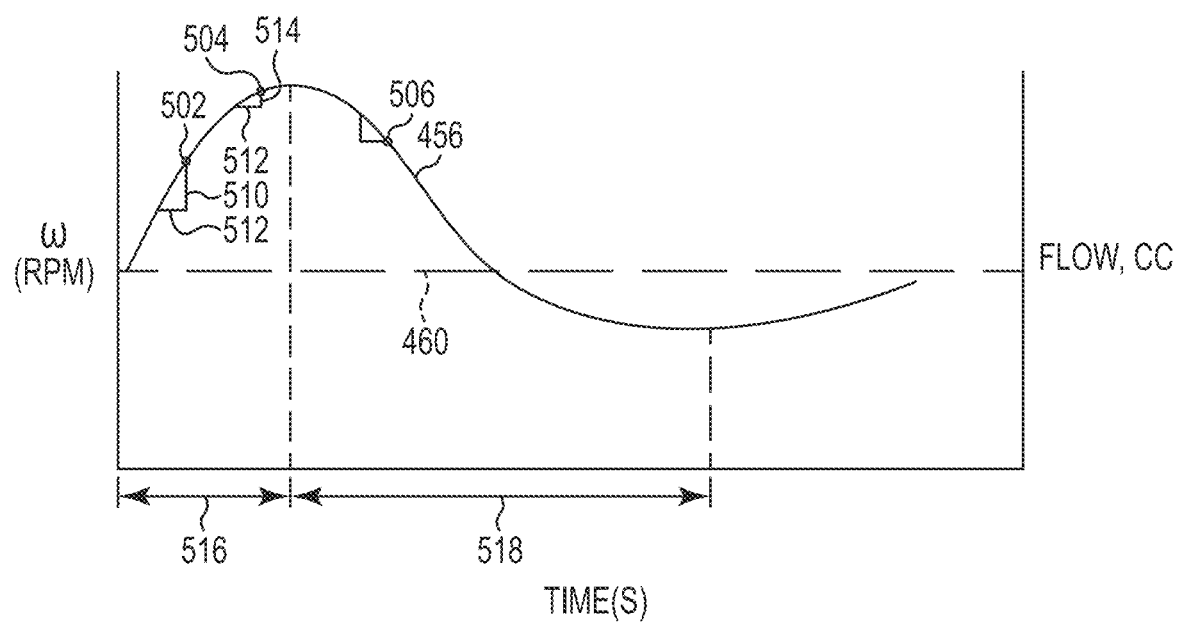
FIG. 8 is another exemplary graph of motor speed and flow versus time, wherein another characteristic of motor speed (e.g., whether speed is increasing or decreasing; and/or a rate of which the motor speed is increasing or decreasing) is illustrated.

While the functional relationship between $F_{est}$ and the speed signal ω may be selected based upon an analysis of the baseline speed as indicated in FIG. 7, other characteristics of the motor/fan speed (e.g., of the speed signal ω) may also be utilized, either alternatively or in addition to the baseline speed, to provide an accurate estimation of flow ($F_{est}$). For example, FIG. 8 illustrates a portion of the exemplary speed signal ω curve 456 (see also FIG. 6A). Due to the shape of the typical curve 456, it may have a different slope at different points along the curve. For example, the slope at a first point 502 may be generally determined by examining a change 510 in the speed signal ω measured over a fixed period of time 512 preceding the first point. As shown in FIG. 8, the slope of the curve 456 may be different (e.g., less) at another point, e.g., point 504, as a change 514 in the speed signal ω at this point is less over the same preceding period of time 512. Accordingly, the characteristic of the speed signal ω used to select the predetermined function may be at least a first range of the detected rate of increase (or decrease) in the rotational speed (i.e., speed signal ω) of the fan 208, or a second range of the detected rate that is different than the first range. Once again, the first range may be associated with a first function (e.g., one or more equations, lookup tables, or matrices), while the second range is associated with a second, different function. Of course, more (or less) than two ranges and their associated functions are certainly possible.

In one embodiment, the analyzer 350 (e.g., the decision element 302 of FIG. 2) may calculate the slope periodically and select the functional relationship between $F_{est}$ and ω based upon the calculated slope being within one of a plurality of ranges (e.g., four ranges corresponding to functions 320, 322, 324, and 326 in FIG. 2). For example, for a slope within a first range, the decision element 302 may select function 320, wherein the constants $A_x$, $B_x$, $C_x$, and $D_x$ in Equation (2) could be set equal to $A_1$, $B_1$, $C_1$, and $D_1$, while a slope within a second range could result in selection of function 322, wherein the constants $A_x$, $B_x$, $C_x$, and $D_x$ could be set equal to $A_2$, $B_2$, $C_2$, and $D_2$ (wherein at least one of the constants with the subscript "1" is different that the respective constant with the subscript "2"). Of course, in other embodiments, an entirely different equation (e.g., linear or other non-linear equation) could be used when the slope is within one or more of the ranges.

In yet another embodiment, the functional relationship between the speed signal ω and $F_{est}$ (e.g., Functions 320, 322, 324, and 326 in FIG. 2) could be selected based upon whether the slope of the speed signal ω curve 456 (see FIG. 8) is positive (e.g., as would be the case for any point along the curve 456 between peak expiration and peak inspiration (in the region 516), e.g., see points 502 and 504 in FIG. 8) or negative (as would be the case for any point along the curve 406 between peak inspiration and peak expiration (in the region 518), see, e.g., third point 506 of FIG. 8).

In still yet other embodiments, the characteristic evaluated to select the predetermined function could be whether the rotational speed of the fan 208 (e.g., the speed signal ω) suggests or is indicative of inspiration or expiration of the user. Stated alternatively, the analyzer 350 could evaluate whether the speed signal ω is above the baseline speed 460 in FIG. 8 (indicating inspiration) or below the baseline speed (indicating expiration) and select a corresponding function based thereon.

Figure 9:
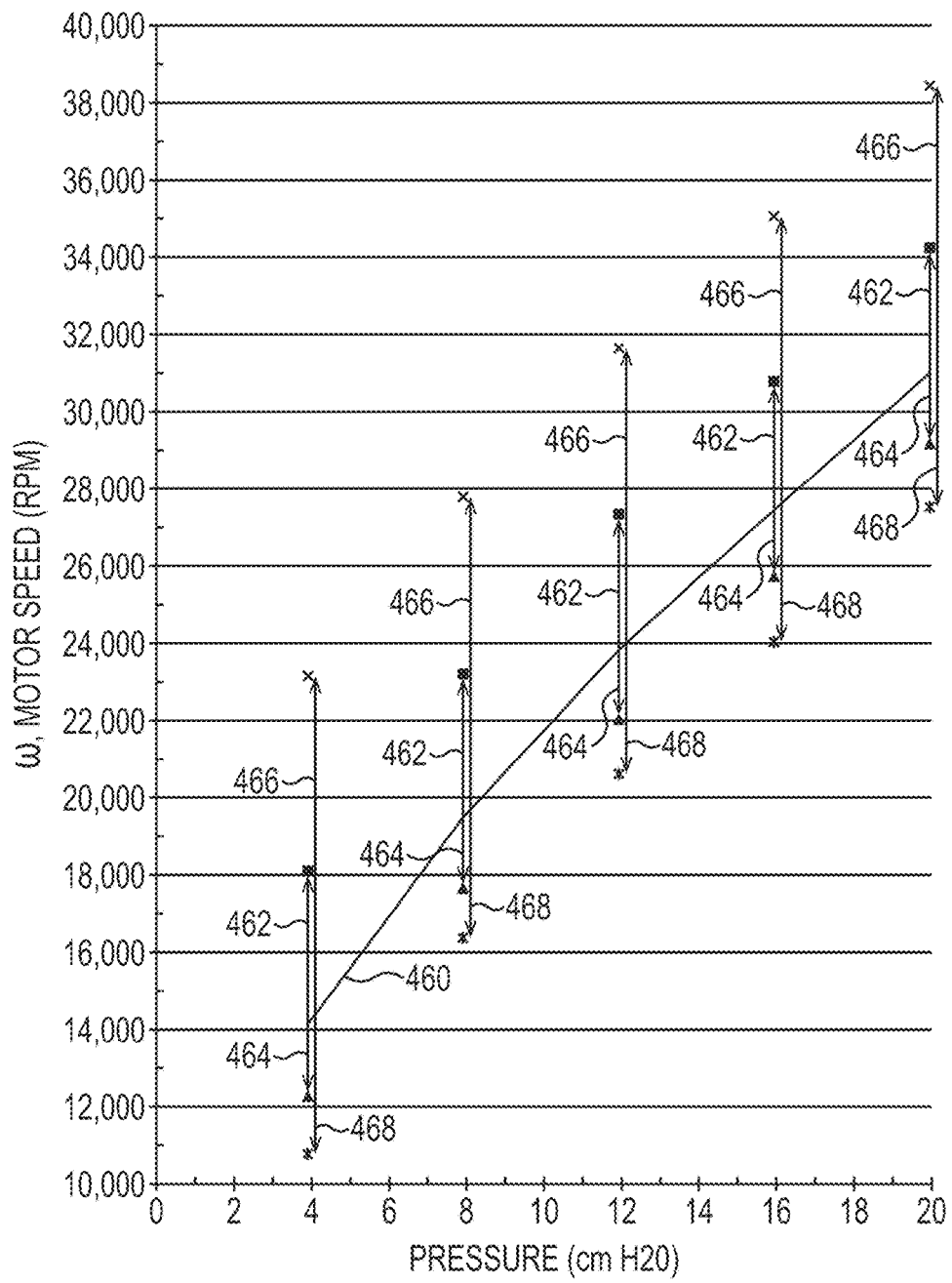
FIG. 9 is an exemplary graph of motor speed versus pressure illustrating potential breaths, at varying treatment pressures and leaks, in accordance with one embodiment of the disclosure.

In still yet another embodiment, the characteristic of the speed signal ω used to select the predetermined function could be the actual rotational speed of the fan (e.g., the magnitude of the speed signal ω) itself. As an example, FIG. 9 plots motor speed v. treatment pressure for different levels of breath flow at one elevation (assuming a constant intentional leak). As shown in this view, the baseline speed for a given intentional vent leak (line 460) may increase with increasing pressure as described elsewhere herein. FIG. 9 further illustrates, for an I:E ratio of 1:1, the variation in motor/fan speed for small breath inspiration (see line 462) and expiration (line 464), as well as for large breath inspiration (line 466) and expiration (line 468). As clearly shown in this view, a breath can cause the motor speed to deviate significantly from the baseline speed. For example, at a pressure of 4 cm $H_2O$, the motor/fan speed may have a baseline speed of about 14,100 RPM, but could slow to about 10,800 RPM during a large expiration, and accelerate to about 23,300 RPM for a large inspiration. With this motor speed variation, it may be beneficial for the analyzer 350 to select the predetermined function for calculating $F_{est}$ based upon the actual instantaneous speed of the motor/fan.

In still yet other embodiments, the characteristics of the speed signal ω used to select the predetermined function could be based upon the type of gas used, the density of the gas, the temperature of the gas, and/or the humidity of the gas. These factors may influence entirely new flow equations, or may simply alter certain values of the constants $A_x$, $B_x$, $C_x$, and $D_x$ in Equation (2).

Figure 10:
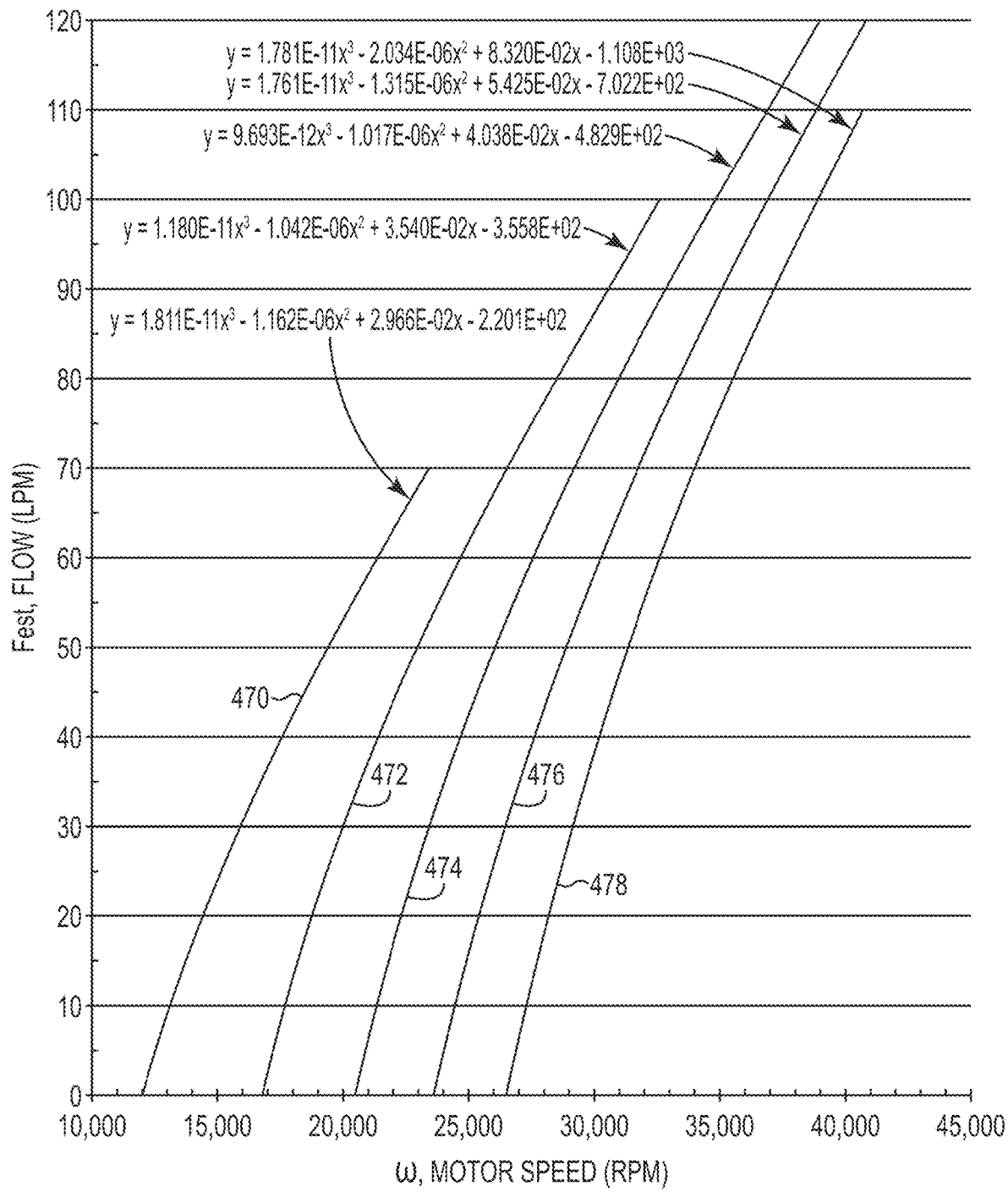
FIG. 10 illustrates exemplary curves for estimated flow versus motor speed for different pressures in accordance with one embodiment.

While not wishing to be bound to any particular embodiment, FIG. 10 illustrate an exemplary flow v. motor speed graph for five different treatment pressures. Once again, these curves are exemplary only and represent only a single functional relationship (e.g., the baseline speed) for each of the identified pressures. Once again, other functional relationships for each pressure are certainly possible.

Moreover, the transfer functions illustrated in FIG. 10 generally depict static conditions concerning speed-to-flow transformation. For example, the transfer functions of FIG. 10 may be influenced by physical parameters of one or both of the motor/fan and the flow path (e.g., PAP apparatus, delivery tube, mask, vent leak, accessory devices in the flow path (e.g., humidifiers), etc.). Accordingly, for a given PAP system (e.g., based upon one or more first or static (e.g., constant flow rate) characteristics), a first transfer function relating constant fan speed to flow rate may be established for any given PAP pressure. When varying or dynamic (e.g., breathing) loads are introduced, the analyzer may evaluate the speed signal and determine a dynamic second characteristic. Based upon this second characteristic, a second transfer function may be selected to equate instantaneous fan speed to flow rate during active breathing as discussed herein (see, e.g., FIG. 8 and accompanying description).

In FIG. 10, the relationship between flow $F_{est}$ (in LPM) and motor speed (in RPM as represented by speed signal ω) may be expressed in accordance with Equation (2) above, wherein the values of $A_x$, $B_x$, $C_x$, and $D_x$ are indicated in Table I below at five different treatment pressures. The equation for each curve is also shown in FIG. 10 (wherein "y" represents $F_{est}$ and "x" represents ω).

TABLE I

| Pressure (cm $H_2O$) | $A_x$ | $B_x$ | $C_x$ | $D_x$ |
|---|---|---|---|---|
| 4 (curve 470) | $1.811 \times 10^{-11}$ | $-1.162 \times 10^{-6}$ | $2.966 \times 10^{-2}$ | $-220.1$ |
| 8 (curve 472) | $1.180 \times 10^{-11}$ | $-1.042 \times 10^{-6}$ | $3.540 \times 10^{-2}$ | $-355.8$ |
| 12 (curve 474) | $9.693 \times 10^{-12}$ | $-1.017 \times 10^{-6}$ | $4.038 \times 10^{-2}$ | $-482.9$ |
| 16 (curve 476) | $1.176 \times 10^{-11}$ | $-1.315 \times 10^{-6}$ | $5.425 \times 10^{-2}$ | $-702.2$ |
| 20 (curve 478) | $1.781 \times 10^{-11}$ | $-2.034 \times 10^{-6}$ | $8.320 \times 10^{-2}$ | $-1108$ |

From the forgoing, it has been discovered that an accurate estimation of PAP system flow ($F_{est}$) may be obtained from the speed signal ω by selecting different predetermined functional relationships ("transfer functions") between $F_{est}$ and ω based upon one or more characteristics of the speed signal ω. While exemplary characteristics of the speed signal are described herein as, among others, the baseline speed, slope magnitude, slope direction (positive or negative), and actual instantaneous motor speed, these characteristics are not limiting. That is, other characteristics of the speed signal ω (e.g., historical or running average speed of the fan) may also be utilized. While FIG. 10 illustrates the flow/motor speed transform equations for different pressures under static conditions, the values of $A_x$, $B_x$, $C_x$, and $D_x$ may be different (or an entirely different equation than that shown in Equation (2) could be used) during dynamic loading (e.g., such as may occur during breathing).

It is contemplated that the functions (e.g., tables, matrices, and/or equations) used by the analyzer 350 to estimate flow may benefit from specific calibration to the particular PAP configuration. For example, specific factors for each PAP apparatus/configuration may change the relationship between motor speed and flow. These factors may include, but are not limited to: the motor configuration used; the impeller design; PAP inlet and outlet flow patterns, including PAP system flow resistance and air turbulence within the PAP; motor drive electronics, including voltage and current capacity; and use of accessories that could impede airflow (e.g., humidifiers). In addition, gas density and environmental conditions (e.g., gas temperature and humidity) may influence the functions utilized.

Figure 11:
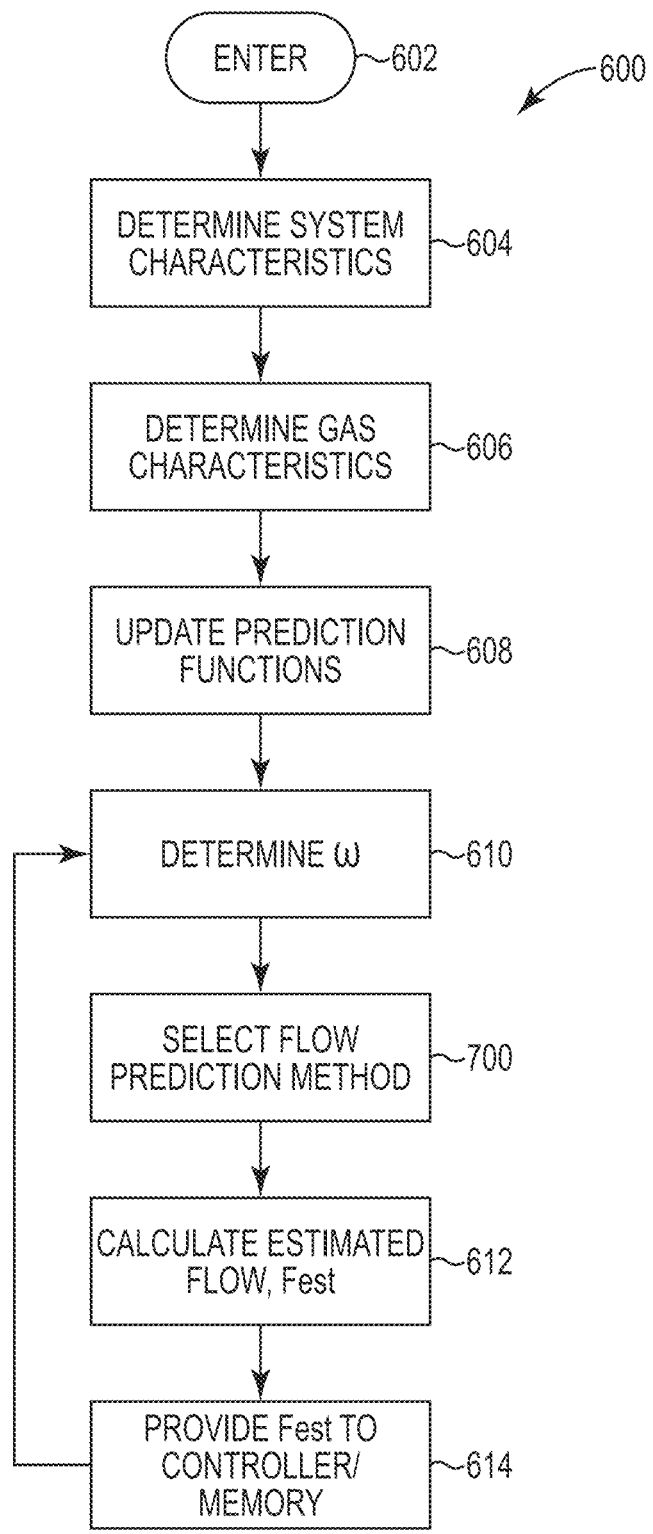
FIG. 11 is a flow chart illustrating operation of a flow estimation algorithm for the apparatus of FIG. 1 in accordance with one embodiment.

FIG. 11 is a flow chart illustrating an exemplary flow estimation algorithm 600 that may be executed by the apparatus 100, e.g., by the analyzer 350. The algorithm is initially started at 602. System characteristics such as motor, impeller, enclosure, hose, target pressure, and mask parameters (as well as parameters regarding accessory devices such as humidifiers) are inputted, measured, or estimated at 604. Gas characteristics (e.g., type or density that may specify temperature and humidity) may be inputted, measured, or estimated at 606 (alternatively, or in addition, actual pressure, and/or pressure delivery errors may be measured at this time). The flow prediction functions based on values provided at 604 and 606 may be updated at 608. The speed of the motor 210/fan 208 (see FIG. 1) is measured at 610 and the resulting speed signal ω is provided to the analyzer 350. Based upon one or more characteristics of the gas type, environmental conditions (e.g., temperature and humidity), and speed of the motor (i.e., the speed signal ω), the analyzer 350 may select a flow prediction function at 700 (e.g., using the decision element 302 of FIG. 2) from a plurality of predetermined functions accessible by the analyzer 350 (see functions 320, 322, 324, and 326 of FIG. 2). One or more of the plurality of predetermined functions may be an equation similar to Equation (2) described above.

Once the flow prediction function is selected at 700, the analyzer 350 may calculate $F_{est}$ by inserting the speed signal ω into the selected flow prediction function at 612 (see also calculation element 304 of FIG. 2). $F_{est}$ may then be provided to other components/aspects of the analyzer 350 (e.g., an apnea/hypopnea prediction algorithm (not shown)) and/or controller 300, or stored in the memory 310 (see FIG. 2) for later analysis at 614. The algorithm may then return to 610 and repeat at a frequency selected to provide a continuous, accurate estimate of system flow (e.g., approximately every 1-50 milliseconds (ms), or more (or less) often).

In some embodiments, the controller and analyzer may receive multiple interrupts per motor shaft rotation (depending on the type of shaft rotation sensor being used). However, as one of skill may appreciate, it may be unnecessary for the analyzer 350 to re-execute the algorithm at every interrupt.

Figures 12, 13:
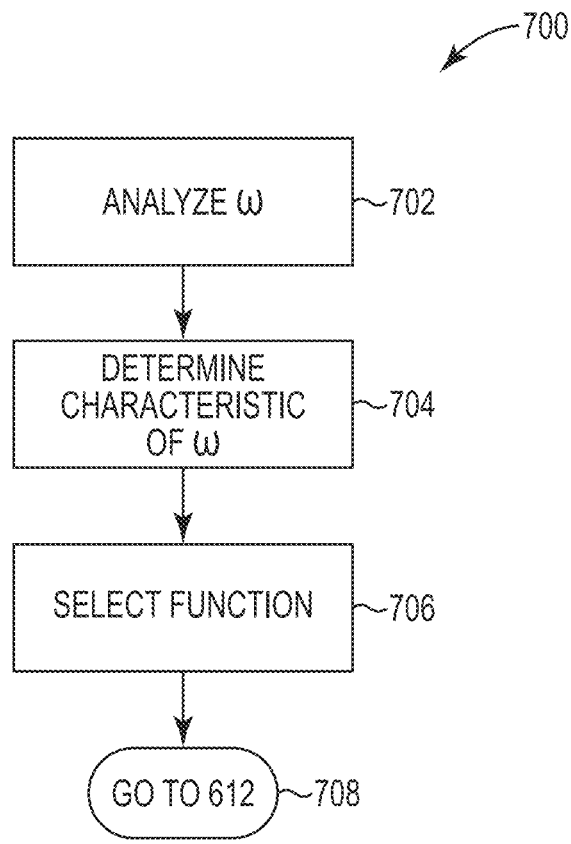
FIG. 12 is an exemplary embodiment of one portion of FIG. 11.
FIG. 13 is a diagrammatic representation of a lookup table that may be used to determine a functional relationship between a speed signal and estimated flow.

FIG. 12 is an expanded view of element 700 of FIG. 11 in accordance with one embodiment. As indicated in this view, the decision element 302 may analyze the speed signal ω and determine a characteristic of the same (e.g., baseline speed, actual speed, slope magnitude, or slope direction of the speed signal ω curve 456 (see FIGS. 7-8)) at 702. The analyzer 350 (e.g., decision element 302) may then analyze the characteristic of the speed signal ω at 704 in order to determine which function of the plurality of predetermined functions will be utilized to estimate flow $F_{est}$. For example, the decision element 302 may examine at 704: the baseline speed and determine which predefined range it falls within; the slope of the speed signal ω curve 406 and determine which predefined range it falls within; the direction of the speed signal ω curve 406 and determine whether it is positive or negative; or the actual instantaneous speed of the motor and determine which predefined range it falls within. While described as analyzing a single criteria (e.g., baseline speed or slope of curve 406), other embodiments may select a predetermined function based upon an analysis of multiple criteria (e.g., on both baseline speed and slope).

Based upon the determination made at 704, the decision element may select the function (see, e.g., 320, 322, 324, or 326 of FIG. 2) at 706 that will be used to correlate the speed signal ω to flow $F_{est}$. Once the equation is selected, control is passed to 612 (at 708) in FIG. 11 for calculation of $F_{est}$.

Once again, while described above as a polynomial function (see Equation (2)), the functional relationship between $F_{est}$ and blower motor speed (the speed signal ω) could alternatively be calculated using more or less sophisticated mathematical equations. For instance, one or more of the predetermined functions could be expressed as: a linear equation, a quadratic (or other polynomial) equation; an exponential or logarithmic equation; a Taylor series; any other non-linear equation, or a combination of any of the above depending upon what equation may best fit the motor speed-to-flow transformation for a given set of PAP operating conditions.

Moreover, while each of the predetermined functions (i.e., the functional relationships between $F_{est}$ and the speed signal ω) are described herein as mathematical formulas executed by the analyzer 350, one or more of the predetermined functions could also be embodied in a matrix or a simple lookup table. An exemplary matrix or lookup table 800 is shown in FIG. 13, wherein for a specific input (speed signal ω), the lookup table would return a value for $F_{est}$. The lookup table may include additional columns (e.g., represented by single column "x" in FIG. 13) of additional data that reflect other parameters of the system for any given motor speed. Such parameters may include, but are not limited to: parameters representative of the motor configuration; the impeller design; PAP inlet and outlet flow patterns, including PAP system flow resistance and air turbulence within the PAP; motor drive electronics, including voltage and current capacity; and use of accessories that could impede airflow (e.g., humidifiers). The lookup table could also include data indicative of, or otherwise influenced by, actual pressure, target pressure, and/or pressure delivery errors. In addition, gas density and environmental conditions (e.g., gas temperature and humidity) may influence the functions utilized. Some aspects of these functions could also include lookup tables, matrices, or functions for inserting flow time delays as appropriate.

While methods and apparatus are described herein as utilizing independent, discrete functions to estimate flow (based on selection of various characteristics of the speed signal), these discrete functions could be incorporated into a single mathematical equation, matrix, or lookup table. That is to say, a single "function" could analyze and determine what flow estimation calculations should be made to generate an accurate flow estimate. In such a case, discrete functions for the various ranges of baseline speed (see FIG. 7) would be addressed by a single mathematical function.

Such a function could also factor in other characteristics of the speed signal (e.g., running average speed, whether the speed is increasing or decreasing, the rate of speed increase or decrease, etc.) to yield a "master" function replacing the individual discrete functions described herein.

As one of skill in the art may appreciate, embodiments described herein may permit accurate estimation of information regarding PAP flow rates without the need for dedicated flow sensors or transducers. Moreover, flow estimation may be accomplished based on a signal representative of the blower speed (speed signal ω) without requiring additional inputs related to the system (e.g., motor power, current draw, etc.). Moreover, the exemplary systems and methods described herein may alter the relationship between flow and measured motor/fan speed based on one or more changing characteristics of the motor/fan speed (speed signal ω). As a result, a potentially more accurate estimation of flow may be realized.

As stated elsewhere herein, providing a signal representative of flow may be beneficial for a variety of reasons. For instance, the estimated flow rate may be used to determine gross mask leaks or the occurrence of sleep disordered breathing (e.g., an apnea or hypopnea). Moreover, in Bi-PAP systems, flow rate may be used to determine transitions between inspiration and expiration. Still further, recorded flow rate may be useful to a health care provider when subsequently evaluating patient compliance and sleep patterns. Still further, flow estimation may be beneficial for predicting when best to energize a rapid response humidifying element (e.g., in order to increase humidity to the patient during inspiration while minimizing humidity to the patient during expiration). Such exemplary humidifier systems and methods are described in US 2015-0165146 to Bowman et al., which is incorporated herein by reference in its entirety.

While described herein with respect to constant pressure PAP apparatus, it is contemplated that other embodiments may find application to systems wherein a variable pressure is provided to the user, e.g., Bi-Level PAP and Auto-PAP as well as devices offering pressure relief during expiration. In fact, embodiments like those described herein may find application to most any system wherein obtaining flow data is desirable without requiring the use of a dedicated flow transducer.

Illustrative embodiments are described and reference has been made to possible variations of the same. These and other variations, combinations, and modifications will be apparent to those skilled in the art, and it should be understood that this disclosure is not limited to the illustrative embodiments set forth herein.

What is claimed is:

1. A positive airway pressure apparatus comprising:
a blower adapted to generate a flow of breathable gas, the blower comprising a motor and a fan rotatable by the motor;
a sensor associated with the blower, the sensor adapted to detect a rotational speed of the fan and generate a speed signal representative of the rotational speed of the fan;
a controller adapted to measure pressure of the flow of breathable gas; and
an analyzer in communication with the controller, wherein the analyzer is adapted to receive the speed signal and estimate a parameter representative of the flow of breathable gas, the parameter determined by inputting the speed signal into a function selected from a plurality of predetermined functions for estimating the parameter representative of the flow of breathable gas, wherein each of the plurality of predetermined functions corresponds to one of a plurality of characteristics associated with the rotational speed of the fan.

2. The apparatus of claim 1, wherein each of the plurality of predetermined functions comprises an equation, a matrix, or a lookup table.

3. The apparatus of claim 1, wherein the sensor comprises at least one of a tachometer, Hall effect sensor, a motor coil voltage sensor, a motor coil current sensor, an electromagnetic field sensor, or an optical sensor.

4. The apparatus of claim 1, wherein a characteristic of the plurality of characteristics comprises a baseline speed of the fan.

5. The apparatus of claim 4, wherein the baseline speed is determined by averaging the speed of the fan over a preceding period of time.

6. The apparatus of claim 4, wherein the baseline speed is determined by the speed of the fan during an apnea.

7. The apparatus of claim 1, wherein a characteristic of the plurality of characteristics comprises an instantaneous speed of the fan.

8. The apparatus of claim 1, wherein a characteristic of the plurality of characteristics comprises a rotational speed of the fan indicative of inspiration or a rotational speed of the fan indicative of expiration.

9. The apparatus of claim 1, wherein a characteristic of the plurality of characteristics comprises a detected increase or detected decrease in the rotational speed of the fan.

10. The apparatus of claim 1, wherein a characteristic of the plurality of characteristics comprises a detected rate of increase or detected rate of decrease in the rotational speed of the fan.

11. The apparatus of claim 10, wherein the detected rate of increase in the rotational speed of the fan comprises a first rate of increase and a second rate of increase, wherein a first function of the plurality of predetermined functions is utilized for the first rate of increase, and a second function of the plurality of predetermined functions, different than the first function, is utilized for the second rate of increase.

12. The apparatus of claim 10, wherein the detected rate of decrease in the rotational speed of the fan comprises a first rate of decrease and a second rate of decrease, wherein a first function of the plurality of predetermined functions is utilized for the first rate of decrease, and a second function of the plurality of predetermined functions, different than the first function, is utilized for the second rate of decrease.

13. The apparatus of claim 1, wherein a characteristic of the plurality of characteristics comprises a pressure of the flow of breathable gas.

14. A method for estimating a flow parameter of a positive airway pressure apparatus, the method comprising:
producing a flow of breathable gas with a blower, the blower comprising a motor and a fan powered by the motor;
generating a speed signal proportional to a rotational speed of the fan;
delivering the speed signal to a flow estimation analyzer;
determining, with the analyzer, a first characteristic of the speed signal;
selecting, with the analyzer, a first function from a plurality of predetermined functions based upon the first characteristic of the speed signal, wherein each function of the plurality of predetermined functions is adapted to correlate the speed signal to a flow rate of the flow of breathable gas; and
estimating, with the first function, the flow rate of the flow of breathable gas.

15. The method of claim 14, further comprising:
determining, with the analyzer, a second characteristic of the speed signal;
selecting, with the analyzer, a second function of the plurality of predetermined functions based upon the second characteristic of the speed signal; and
estimating, with the second function, the flow rate of the flow of breathable gas.

16. The method of claim 15, wherein determining the first or second characteristic of the speed signal comprises determining the first or second characteristic when the flow of breathable gas is constant.

17. The method of claim 15, wherein determining the first or second characteristic of the speed signal comprises determining the first or second characteristic when the flow of breathable gas varies.

18. The method of claim 15, wherein determining the first or second characteristic of the speed signal comprises determining whether the speed signal is indicative of inspiration or expiration.

19. The method of claim 15, wherein determining the first or second characteristic of the speed signal comprises determining a rate of increase or a rate of decrease of the speed of the fan.

20. The method of claim 15, wherein determining the first or second characteristic of the speed signal comprises determining an average or baseline speed of the fan during a previous period of time.

21. The method of claim 20, wherein determining the baseline speed of the fan comprises determining whether the baseline speed of the fan is within at least a first range or a second range.

22. The method of claim 14, further comprising detecting a mask leak based, at least in part, upon the estimated flow rate.

23. The method of claim 14, further comprising detecting an apnea or hypopnea based, at least in part, upon the estimated flow rate.

24. The method of claim 14, wherein estimating the flow rate comprises estimating the flow rate using one or more independent linear relationships between the flow rate and the speed signal.

25. The method of claim 14, wherein estimating the flow rate comprises estimating the flow rate using one or more independent non-linear relationships between the flow rate and the speed signal.

26. The method of claim 14, wherein estimating the flow rate comprises estimating the flow rate using a lookup table of the flow rate based upon the speed signal.

* * * * *